US009623253B2

(12) United States Patent
Perryman et al.

(10) Patent No.: US 9,623,253 B2
(45) Date of Patent: Apr. 18, 2017

(54) DEVICES AND METHODS FOR TREATING UROLOGICAL DISORDERS

(71) Applicant: MICRON DEVICES, LLC, Miami Beach, FL (US)

(72) Inventors: Laura Tyler Perryman, Miami Beach, FL (US); Chad Andresen, Miami Beach, FL (US)

(73) Assignee: Micron Devices, LLC, Miami Beach, FL (US)

( * ) Notice: Subject to any disclaimer, the term of this patent is extended or adjusted under 35 U.S.C. 154(b) by 0 days.

(21) Appl. No.: 14/775,429

(22) PCT Filed: Mar. 14, 2014

(86) PCT No.: PCT/US2014/029683
§ 371 (c)(1),
(2) Date: Sep. 11, 2015

(87) PCT Pub. No.: WO2014/153219
PCT Pub. Date: Sep. 25, 2014

(65) Prior Publication Data
US 2016/0023005 A1    Jan. 28, 2016

Related U.S. Application Data

(63) Continuation-in-part of application No. PCT/US2013/073326, filed on Dec. 5, 2013, and a
(Continued)

(51) Int. Cl.
A61N 1/00    (2006.01)
A61N 1/372    (2006.01)
(Continued)

(52) U.S. Cl.
CPC ....... *A61N 1/37229* (2013.01); *A61N 1/3606* (2013.01); *A61N 1/3787* (2013.01); *A61N 1/37205* (2013.01)

(58) Field of Classification Search
CPC .............. A61N 1/37229; A61N 1/3606; A61N 1/37205; A61N 1/3787
See application file for complete search history.

(56) References Cited

U.S. PATENT DOCUMENTS 7,236,822 B2    6/2007   Dobak
7,283,867 B2    10/2007  Strother et al.
(Continued)

FOREIGN PATENT DOCUMENTS

WO    WO2005/058415    6/2005
WO    WO2006/029007    3/2006
(Continued)

OTHER PUBLICATIONS

Authorized officer Shane Thomas, International Search Report and Written Opinion in PCT/US2014/029683, mailed Jul. 30, 2014, 30 pages.
(Continued)

*Primary Examiner* — Robert N Wieland
(74) *Attorney, Agent, or Firm* — Fish & Richardson P.C.

(57) ABSTRACT

Some implementations provide a method for treating urological disorders in a patient, the method including: placing an introducer into a patient's body through an incision site on the patient's body, the patient suffering from an urological disorder; placing an implantable wireless device into an inner lumen of the introducer, the implantable wireless device suitable to fit into the inner lumen and configured to receive electromagnetic energy non-inductively from a source located outside the patient's body; through the inner lumen of the introducer, positioning the implantable wireless
(Continued)

device adjacent to or near one or more excitable tissue in the patient, the one or more excitable tissue regulating a nerve activity associated with the urological disorder; and causing neural modulation of the one or more excitable tissue through one or more electrodes on the implantable wireless device.

17 Claims, 28 Drawing Sheets

Related U.S. Application Data continuation-in-part of application No. 13/551,050, filed on Jul. 17, 2012, now Pat. No. 9,409,030, and a continuation-in-part of application No. 13/562,221, filed on Jul. 30, 2012, now Pat. No. 9,199,089, and a continuation-in-part of application No. 13/584,618, filed on Aug. 13, 2012, now Pat. No. 8,849,412, and a continuation-in-part of application No. 13/621,530, filed on Sep. 17, 2012, now Pat. No. 9,242,103, and a continuation-in-part of application No. 14/045,764, filed on Oct. 3, 2013, now Pat. No. 9,220,897.

(60) Provisional application No. 61/786,181, filed on Mar. 14, 2013.

(51) Int. Cl.
*A61N 1/36* (2006.01)
*A61N 1/378* (2006.01)

(56) References Cited

U.S. PATENT DOCUMENTS

| | | | |
|---|---|---|---|
| 8,190,267 | B2 | 5/2012 | Greenburg et al. |
| 2005/0240229 | A1 | 10/2005 | Whitehurst et al. |
| 2007/0065525 | A1* | 3/2007 | Lee .......................... A21D 2/14 424/728 |
| 2007/0239224 | A1 | 10/2007 | Bennett et al. |
| 2008/0234598 | A1* | 9/2008 | Snyder ................. A61B 5/0006 600/545 |
| 2009/0118780 | A1* | 5/2009 | DiLorenzo ......... A61N 1/37247 607/2 |
| 2010/0179562 | A1 | 7/2010 | Linker et al. |
| 2011/0301662 | A1* | 12/2011 | Bar-Yoseph ......... A61N 1/0514 607/40 |
| 2012/0143282 | A1 | 6/2012 | Fukui et al. |
| 2012/0323294 | A1 | 12/2012 | Laing et al. |
| 2014/0046413 | A1* | 2/2014 | Kane .................... A61N 1/0558 607/116 |

FOREIGN PATENT DOCUMENTS

| | | |
|---|---|---|
| WO | WO2007/059386 | 5/2007 |
| WO | WO2009/045772 | 4/2009 |
| WO | WO2009/132091 | 10/2009 |
| WO | WO2012/003140 | 1/2012 |
| WO | WO2012/103519 | 8/2012 |
| WO | WO2012/138782 | 10/2012 |

OTHER PUBLICATIONS

International Search Report and Written Opinion in International Application No. PCT/US2013/073326, mailed Aug. 6, 2014, 18 pages.

International Preliminary Report on Patentability in International Application No. PCT/US2013/073326, dated Jun. 9, 2015, 13 pages.

* cited by examiner

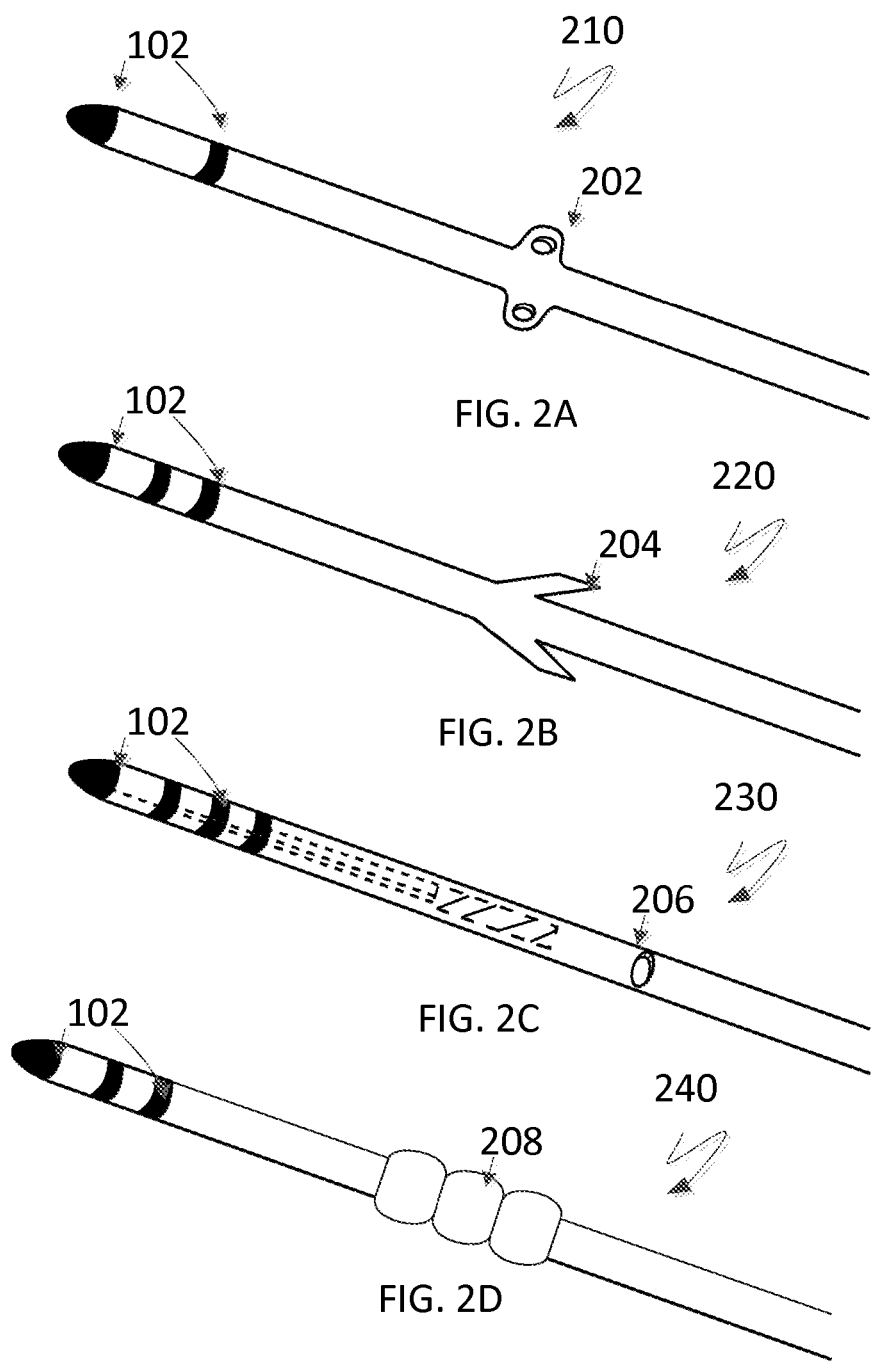

DEVICES AND METHODS FOR TREATING UROLOGICAL DISORDERS

CROSS REFERENCE TO RELATED APPLICATIONS

This application claims benefit of U.S. provisional Patent Application 61/786,098, filed Mar. 14, 2013. Under 35 U.S.C. 365 and 120, this application claims the benefit of and is a continuation in part of PCT application PCT/US2013/073326, filed Dec. 5, 2013, U.S. patent application Ser. No. 13/551,050 filed Jul. 17, 2012, U.S. patent application Ser. No. 14/045,764 filed Oct. 3, 2013, U.S. patent application Ser. No. 13/562,221, filed Jul. 30, 2012, U.S. patent application Ser. No. 13/584,618, filed Aug. 13, 2012 and U.S. patent application Ser. No. 13/621,530, filed Sep. 17, 2012. The disclosures of all of these applications are incorporated by reference in their entirety for all purposes.

TECHNICAL FIELD

This application relates to the delivery of energy impulses (and/or fields) to bodily tissues for therapeutic purposes.

BACKGROUND

Modulation of neural tissue in the body by electrical stimulation has become an important type of therapy for patients with chronic disabling conditions, including chronic pain, problems of movement initiation and control, involuntary movements, vascular insufficiency, heart arrhythmias, craniofacial pain and more. A variety of therapeutic intra-body electrical stimulation techniques can treat these conditions. Typically, such devices utilize a subcutaneous battery operated implantable pulse generator (IPG) to provide power or other charge storage mechanisms. However, devices which utilize a battery-powered or charge storage component, are no longer functional once the battery cannot be recharged or charge cannot be stored. Consequently, for an implanted device, a patient would need to undergo a subsequent surgical procedure to obtain a functional replacement device.

SUMMARY

In one or more aspects, implementations may utilize a system for treating urological disorders. The system may include one or more implantable electrodes powered from an remote source configured to apply one or more electrical impulses to a neural tissue, particularly nerves associated with urinary pain, incontinence, erectile dysfunction or other urological disorders, such as the tibial nerve in the patient's ankle, the pudendal nerve, sciatic nerve, superior gluteal nerve, lumbo-sacral trunk, inferior gluteal nerve, common fibular nerve, posterior femoral cutaneous nerve, obturator nerve, common peroneal nerve, plantar nerve, sacral nerves S1, S2, S3, or S4, or nerves of the S1, S2, S3, or S4 dermatome, and sacral anterior root nerves. Applicable sites of stimulation may include: urethral sphincter and pelvic floor muscles, the suprapubic area, rectum or anus, vagina or clitoris, penis, perineum, thigh, and foot.

The electrical pulses may modulate nerves to treat urological disorders. The electrical pulses are generated from electrodes integrated into an implantable wireless device that is coupled to a remote pulse generator to provide power. The implantable wireless device is part of a treatment system that may include a first antenna integrated into the implantable wireless device for receiving an input signal from a second antenna, remote from the first antenna. The second antenna may be external to the patient's body or it may be positioned on the patient's body or implanted within the patient's body remotely from the first antenna on the implantable wireless device. The second antenna may be located on an external pulse generator, different and separate from the implantable wireless device. In some implementations, the second antenna is configured to transmit the input signal, which includes the electrical pulses and electrical power, to the first antenna on the implanted wireless device contained within the patient's body. The first antenna is configured to receive the input signal. Electronic circuitry may be coupled to the first antenna and located on the implanted wireless device. The electronic circuitry may be configured to extract the electrical pulses from the received input signal. The electronic circuitry may provide the electrical pulses to one or more electrodes of the implanted wireless device. In this manner, the electrical pulses may be applied one or more excitable tissue adjacent to or near the one or more electrodes attached to the device. In one configuration, the one or more electrodes and the antenna are housed within an enclosure. The enclosure may be configured for subcutaneous placement on the patient's body or percutaneous placement within the patient's body. The placement of the implanted wireless device may be accomplished by the use of an introducer. The placement of the implanted wireless device may be guided by fluoroscopy, including X-Ray and ultrasound, to verify that the introducer and needle location are in the correct position.

In some implementations, an input signal containing electrical energy may be delivered to a first antenna contained within the body of the implanted wireless device. The input signal may be converted to electrical pulses, which may then be applied to the electrodes for modulating the nerves at the target site. In one aspect, the input signal is transmitted from a second antenna physically separate from the first antenna and positioned either external to the patient's body or in a location on or in the patient's body separate from the electrodes and the first antenna. In some cases, the implanted wireless device is surgically implanted at the target site. In other cases, the implanted wireless devices are percutaneously advanced to the target site.

In another aspect, some implementations provide a method for treating urological disorders in a patient, the method including: placing an introducer into a patient's body through an incision site on the patient's body, the patient suffering from an urological disorder; placing an implantable wireless device into an inner lumen of the introducer, the implantable wireless device suitable to fit into the inner lumen and configured to receive electromagnetic energy non-inductively from a source located outside the patient's body; through the inner lumen of the introducer, positioning the implantable wireless device adjacent to or near one or more excitable tissue in the patient, the one or more excitable tissue regulating a nerve activity associated with the urological disorder; and causing neural modulation of the one or more excitable tissue through one or more electrodes on the implantable wireless device.

Implementations may include one or more of the following features. Placing the introducer may include placing the introducer through the incision site into a sacral region of the patient. Positioning the implantable wireless device may include positioning the implantable wireless device adjacent to or near a sacral nerve of the patient. Placing the introducer comprises placing the introducer through the incision site into a pelvic region of the patient. Positioning the implantable wireless device may include positioning the implantable wireless device adjacent to a pudendal nerve or branches thereof. Positioning the implantable wireless device may include positioning the implantable wireless device adjacent to or near a prostatic plexus of the patient. positioning the implantable wireless device may include positioning the implantable wireless device adjacent to or near a sacral splanchnic nerve of the patient. Positioning the implantable wireless device may include positioning the implantable wireless device adjacent to or near a cavernous nerve of the patient. Placing the introducer may include placing the introducer percutaneously through an incision site on the patient's lower extremity. Positioning the implantable wireless device may include placing the implantable wireless device adjacent to or near a tibial nerve of the patient. Placing the implantable wireless device further comprises placing the wireless electrode lead into the inner lumen of the introducer having a size of 14 gauge or under.

The method may include using X-Ray fluoroscopy to guide positioning the wireless electrode lead adjacent to or near one or more excitable tissue. The method may include using ultrasound sonography to guide positioning the implantable wireless device adjacent to or near one or more excitable tissue. The method may include withdrawing the implantable wireless device from the patient after the neural modulation.

Causing the neural modulation may include causing an input signal to be transmitted from an external antenna outside the patient's body, the input signal including electrical power and excitation pulses to drive the one or more electrodes of the implantable wireless device; causing the input signal to be received non-inductively by one or more antennas on the implantable wireless device; causing the electrical power and excitation pulses to be extracted from the input signal; and based on the electrical power, causing the excitation pulses to be delivered to the one or more electrodes on the implantable wireless device.

Placing an implantable wireless device may further include placing an implantable wireless device that includes (i) one or more non-inductive antennas configured to receive electromagnetic energy radiated from a source located outside of the patient's body, (ii) electronic circuitry coupled to each of the one or more non-inductive antennas and configured to extract electric power and excitation pulses from the radiated electromagnetic energy as received by the one or more non-inductive antennas, and (iii) one or more electrodes configured to deliver the excitation pulses to the one or more excitable tissue to effectuate neural modulation thereof. Placing the implantable wireless device may further include placing the implantable wireless device that includes at least one of: a spiral electrode, a cuff electrode, a steroid eluting electrode, a wrap-around electrode, a linear electrode, or a hydrogel electrode.

Some implementations may include a method for treating overactive bladder and/or urinary incontinence. The method may include positioning the electrodes of the implanted wireless device adjacent to or near one or more of the nerves in or around the sacral plexus. The method may further include transmitting an input signal from an external antenna outside of the patient's body to one or more antennas within the implanted wireless device. The input signal may include power and information containing electrode polarity setting and electrical pulses for driving the electrodes. The method may further include receiving the input signal, extracting the polarity setting information and electrical pulses, and applying the electrical pulses through the electrodes to the targeted nerves. The electrical pulses may be sufficient to treat the patient's overactive bladder or incontinence.

Some implementations may include a method for treating incontinence. The method may include positioning an electrode from the wireless device adjacent to or near a tibial nerve in a patient and transmitting an input signal from an external antenna to the implanted wireless device. The input signal may include power and information containing waveform parameters to generate an electric field from the electrodes of the implanted wireless device. The method may further include receiving the input signal, extracting the electrical pulses, and applying electrical pulses to one or more electrodes on the implanted wireless device to modulate the tibial nerve sufficiently to treat the incontinence.

Some implementations may include a method for treating erectile dysfunction. The method may include positioning an implanted wireless device adjacent to or near the cavernous nerve or the pudendal nerve and transmitting an input signal to the implanted wireless device from an external controller. The input signal may include power and information containing waveform parameters to generate an electric field from the electrodes of the implanted wireless device. The method may further include receiving the input signal, extracting the electrical pulses and applying electrical impulses to one or more electrodes on the electrode lead to modulate the cavernous or pudendal nerve and treat the erectile dysfunction.

Some implementations may include a method for treating prostatitis or chronic pelvic pain. The method may include positioning an implanted wireless device adjacent to or near stimulation the pudendal nerve, the prostatic plexus or the sacral splanchnic nerve and transmitting an input signal to the implanted wireless device from an external controller. The input signal may include power and information containing electrical pulses for driving the electrodes on the implanted wireless device. The method may include receiving the input signal and applying electrical impulses to one or more electrodes to modulate the targeted nerves and treat the prostatitis or chronic pelvic pain.

The methods described above may include providing an implanted wireless device including an enclosure that houses: one or more electrodes; a first antenna configured to receive, from a second antenna and through electrical radiative coupling, an input signal containing electrical energy, the second antenna being physically separate from the implanted wireless device; one or more flexible circuits electrically connected to the first antenna, the flexible circuits configured to: create the one or more electrical pulses suitable to be applied at the electrodes using the electrical energy contained in the input signal; and supply the one or more electrical pulses to the one or more electrodes, and implanting the wireless device into a patient's body through an introducer.

In another aspect, a system for stimulating neural tissue comprises a controller module having a first antenna external to the patient's body and configured to send an input signal containing electrical energy to a second antenna through electrical radiative coupling. The second antenna is a dipole antenna and is located in an enclosure in a implanted wireless device, such as those described above. The implanted wireless device may not include an internal power source. The circuits of the implanted wireless device may include only passive components. The input signal has a carrier frequency in the range of about 300 MHz to about 8 GHz, preferably between about 750 MHz to about 2.5 GHz.

In another implementation, an implanted wireless device configured for stimulating nerves, such as those described above, preferably comprises an enclosure shaped and configured for percutaneous delivery into a patient's body through an introducer or needle to a target site in the patient's body. The enclosure houses one or more electrodes configured to apply one or more electrical pulses to a neural tissue. The enclosure preferably also houses a first antenna configured to receive, from a second antenna through electrical radiative coupling, an input signal containing electrical energy. In the preferred embodiments, the second antenna is physically separate from the implanted wireless device and may be positioned external to the patient's body. In certain exemplary embodiments, the first antenna is a dipole antenna. The enclosure further comprises one or more circuits electrically connected to the first antenna and configured to create the one or more electrical pulses suitable for stimulation of the neural tissue using the electrical energy contained in the input signal and to supply the one or more electrical pulses to the one or more electrodes of the implanted wireless device.

In one example, a portion of the enclosure may leave the electrodes in a non-direct contact with the neural tissue after the implanted wireless device has been delivered into the patient's body. The enclosure can be semi-cylindrical in shape and the electrodes may include at least one directional electrode that directs a current path associated with the one or more electrical pulses to a direction that is substantially perpendicular to the neural tissue. The electrodes may include a semi-cylindrical array of electrodes. The electrodes may be made of at least one of platinum, platinum-iridium, gallium-nitride, titanium-nitride, iridium-oxide, or combinations thereof. The electrodes may include two to sixteen electrodes, each having a longitudinal length between about 0.25 and 6.0 mm and a diameter between about 0.1 and 0.8 mm. The electrodes are spaced between about 0.25 mm to 6 mm apart and have a combined surface area of between about 0.06 $mm^2$ to 250.0 $mm^2$.

In some cases, the enclosure comprises a feature allowing for mating of a stylet that does not extend the length of the implanted wireless device. The stylet-mating feature can be concave on the proximal portion of the device with a length of between about 0.1 mm and 1.0 mm. The stylet-mating feature may be semi-spherical or may be an asymmetrical shape for further steerability of the device. The enclosure may further include a distal tip. The distal tip can be rounded with a length of between about 0.1 mm and 2.0 mm. The distal tip can also be pointed with a length of between about 0.1 and 6.0 mm. The enclosure may have an external coating of biocompatible polymer, the polymer includes at least one of polymethymethacrylate (PMMA), polydimethylsiloxane (PDMS), parylene, polyurethance, polytetrafluoroethylene (PTFE), or polycarbonate. The enclosure may further have an external coating of silicone elastomer. The enclosure can further house antenna coupling contacts, the antenna contacts being electrically connected to the antennas and the circuit and configured to couple the antenna with the surrounding tissue. The antenna coupling contacts can include two to eight antenna-coupling pairs. The antenna coupling contacts may be located proximal, relative to the electrodes, in the enclosure. The antenna coupling contacts can each have a longitudinal length of between about 0.25 mm and 6.0 mm, and a diameter of between about 0.1 mm to 0.8 mm. The antenna coupling contacts can be spaced between about 10 mm and 80 mm apart. At least one of the antennas can be constructed as a conductive trace contained on one of the circuits. At least one of the antennas can be fabricated as a conductive wire connected to one of the circuits. The circuits can be flexible circuits. The flexible circuits are capable of undergoing a bend radius of under 0.5 mm. The flexible circuits can be placed proximal, relative to the electrodes, in the enclosure. The flexible circuits can include a waveform conditioning circuit.

In yet another aspect, a stylet can be configured to aid in the surgical placement of the implanted wireless device. The stylet fits through the inner diameter of a touchy needle no greater than 14 gauge, and may contain a feature for mating the stylet to an implanted wireless device. On the distal tip of the stylet is a mating feature, which may be semi-spherical, and grips the implanted wireless device during placement. Other features may include alternative extruded shapes for mating the stylet to the stimulator electrode lead. The mating feature may only extrude from the distal tip of the stylet from between about 0.1 mm and 1.0 mm and does not fill the body of the device. The mate between the implanted wireless device and the stylet is active only during distal directional movement of the stylet. The stylet may have a longitudinal length of between about 50 mm and 177 mm. The stylet may have a diameter in the range from between about 0.1 mm and 0.9 mm. The stylet may be made of a rigid biocompatible material such as stainless steel, titanium, nylon, or polyethylene. The mating feature may have a surface material that allows for increased friction such as silicon or polyurethane to improve the mate between the stylet and the implanted wireless device.

Some implementations of the stylet include a central lumen that contains a plunger used for creating a negative pressure port on the distal tip. The negative pressure port exits where the mating feature connects to the implanted wireless device. This suction stylet can grip the implanted wireless device during distal and proximal directional movement. The suction stylet may have a locking feature that allows for the plunger pressure level to be maintained without the operator maintaining the force on the plunger.

BRIEF DESCRIPTION OF THE DRAWINGS

FIG. 2A-2D depict leads with various types of suturing features.

DETAILED DESCRIPTION OF THE INVENTION

Figure 1:
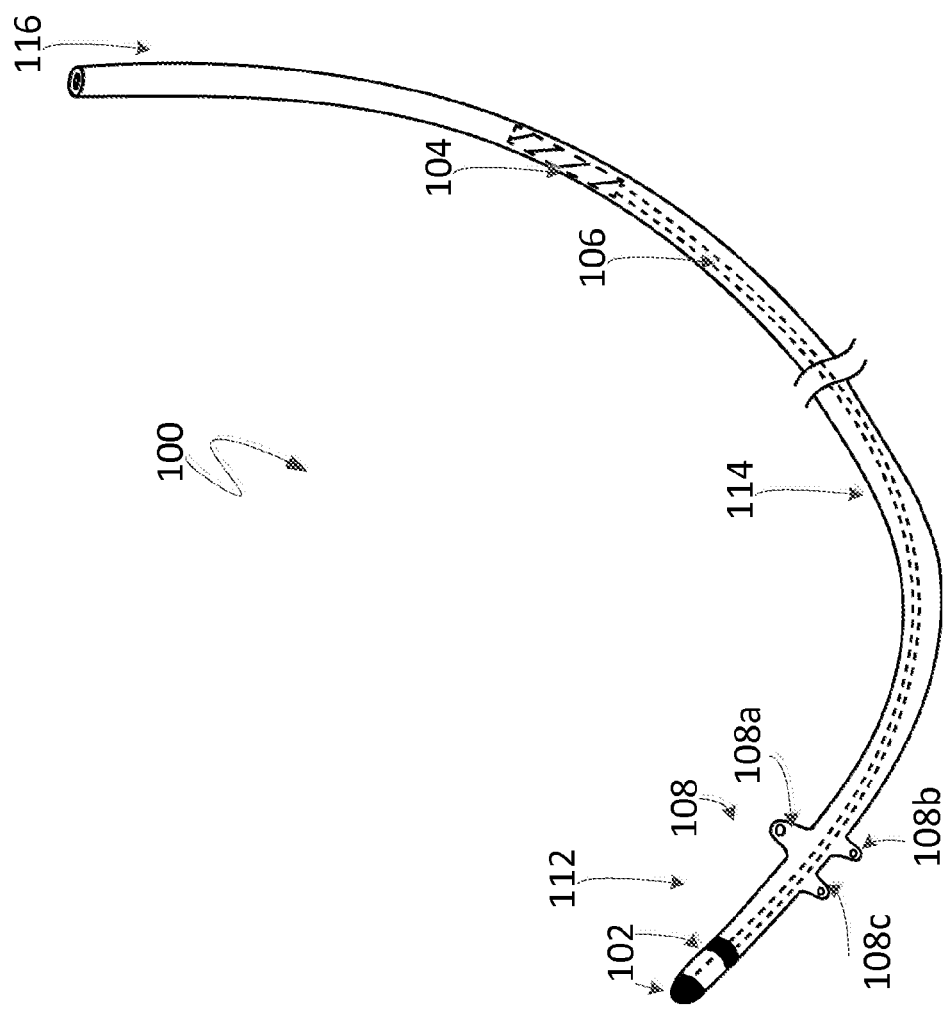
FIG. 1 illustrates an example of an implantable lead.

In various implementations, a neural stimulation system is used to apply one or more electrical impulses to targeted nerves for treating urological disorders, such as overactive bladder, urge incontinence, stress incontinence, fecal incontinence, urge frequency, non-obstructive urinary retention (ischuria), urinary pain, erectile/sexual disorders, non-obstructive urinary retention and interstitial cystitis/painful bladder syndrome and the like. The targeted nerves can include, but are not limited to, the tibial nerve in the patient's ankle, the pudendal nerve, sciatic nerve, superior gluteal nerve, lumbo-sacral trunk, inferior gluteal nerve, common fibular nerve, posterior femoral cutaneous nerve, obturator nerve, common peroneal nerve, plantar nerve, sacral nerves S1, S2, S3, or S4, or nerves of the S1, S2, S3, or S4 dermatome, and sacral anterior root nerves. Applicable sites of stimulation may include: urethral sphincter and pelvic floor muscles, the suprapubic area, rectum or anus, vagina or clitoris, penis, perineum, thigh, and foot.

Various implementations can include distinct advantages over wired leads with regard to ease of insertion, cross connections, elimination of extension wires, and no requirement for an implantable pulse generator in order to administer a chronic therapy. Various implementations also may have an associated lower overall cost compared to existing implantable neural modulation systems due to the elimination of the implantable pulse generator and this may lead to wider adoption of neural modulation therapy for patients as well as reduction in overall cost to the healthcare system.

The storage (continence) and voiding (micturition) of urine are performed by the urinary bladder and urethra, which are muscular structures controlled by the nervous system. The lower urinary tract has two phases of activity: the storage phase, when urine is stored in the bladder, and the voiding phase, when urine is released through the urethra. The urethra has two sphincters, an internal smooth muscle sphincter and an external skeletal muscle sphincter. During the storage phase, the sphincters of the urethra contract (blocking flow of urine), and the detrusor smooth muscle of the bladder wall is relaxed. During the voiding phase, the reverse happens—the sphincters of the urethra relax, permitting flow of urine, and the detrusor muscle of the bladder contracts to force urine out through the urethra.

Nerve signals from stretch-sensitive receptors' in the bladder wall are sent via the spinal cord to the pontine micturition center in the brainstem and to the cerebrum where voluntary actions are initiated. When the bladder fills and the bladder's stretch-sensitive receptors are actively signaling a filled state, the conscious urge to urinate becomes difficult to ignore. Once the voluntary nerve signal to begin urination has been issued, that signal is sent from the brain via the spinal cord to the lower urinary tract, causing the smooth muscle of the bladder to contract and the urethral sphincter muscle to relax. The flow of urine through the urethra is then sensed by its receptors, and the receptors send nerve signals which help sustain urination until the bladder is empty and the storage phase begins again.

Urinary incontinence is defined by the International Continence Society as "the complaint of any involuntary leakage of urine." There are several types of incontinence, the most common being stress, urge, and overflow incontinence. Stress incontinence is the loss of small amounts of urine as the result of coughing, laughing, sneezing, exercising or other movements that increase intra-abdominal pressure. Urge incontinence is the involuntary loss of urine while suddenly feeling the need or urge to urinate, which is often associated with overactive bladder. Overflow (dribbling) incontinence usually occurs when the patient's bladder is always full so that it frequently leaks urine. It is often caused by obstruction of the urethra, e.g. by an enlarged prostate, but may be associated with non-obstructive urinary retention as well.

Individuals with an overactive bladder exhibit a sudden urge to urinate and a high frequency of urination, especially at night (nocturia). They often, but not always, also exhibit urge incontinence that is associated with the leakage of urine due to bladder muscles that contract or spasm inappropriately. Often these contractions occur regardless of the amount of urine that is in the bladder. Urge incontinence may result from bladder outlet obstruction from an enlarged prostate, inflammation or infection, or neurological disorders, as described below. However, in most cases of urge incontinence, no specific cause can be identified.

Individuals with urge incontinence and mixed incontinence (stress and urge incontinence combined) have overactive bladder (OAB), because they exhibit sudden urges to urinate. The prevalence of OAB is approximately 11-19% in men and 13-17% in women. OAB prevalence increases with age and tends to be more prevalent in women at ages less than 60 years but more prevalent in men at ages greater than 60. In the year 2000, the costs in the United States for treating urinary incontinence and overactive bladder were estimated to be 19.5 and 12.6 billion dollars, respectively, taking into account costs associated with diagnosis and treatment, as well as consequent costs such as predisposition to urinary tract infections, ulcers, perineal rashes and other skin conditions, infections, falls and broken bones, and premature nursing home admissions. Psychologically, overactive bladder and incontinence are associated with embarrassment, isolation, stigmatization, depression, and the fear of institutionalization.

Management options for overactive bladder include lifestyle adjustments, bladder retraining, pelvic floor exercises, biofeedback, and pharmacotherapy (e.g., anticholinergic antimuscarinic medications as the mainstay of treatment, such as oxybutynin, tolterodine, trospium chloride, derifenacin, solifenacin, and fesoterodine fumarate). However, side effects and urinary retention occur in approximately 20% of those who use these medications. In other patients, the medications are ineffective, such that 75% of patients discontinue the use of anticholinergic medications within one year. Major surgical procedures (e.g., bladder augmentation, Burch colposuspension and the pubovaginal sling) are considered last resorts for certain types of incontinence, as they potentially lead to serious side effects. Having failed conservative and drug-based therapies for incontinence, some patients resign themselves to a lifetime of containment devices and pads, rather than resort to surgery If pharmacotherapy is unsuccessful and surgery is not being considered, patients with an overactive bladder or incontinence have been increasingly treated by neuromodulation. Many nerves at many anatomical locations have been electrically stimulated in an attempt to treat such urological disorders. Attempts have been made to improve bladder function by stimulating: the bladder wall via a catheter (intravesical stimulation), the bladder directly, the pudendal nerve (transvaginally or using an anal plug or on the perineum or on the clitoris or on the penis or on the periurethral muscle), on a suprapubic area transcutaneously, over the S2 or S3 dermatome transcutaneously, on the tibial nerve transcutaneously or percutaneously, on the sacral spine directly, on the sacral anterior root, on the thigh muscle, and on the foot.

Sacral nerve electrical stimulation is a form of neuromodulation that is used to treat overactive bladder and incontinence. Humans have 31 left-right pairs of spinal nerves, each roughly corresponding to a segment of the vertebral column: 8 cervical spinal nerve pairs (C1-C8), 12 thoracic pairs (T1-T12), 5 lumbar pairs (L1-L5), 5 sacral pairs (S1-S5) and 1 coccygeal pair. Sacral nerve modulation was developed based on the observation that the S2-S4 nerve roots provide the primary innervation to the bladder and urethra. With sacral nerve modulation, patients first undergo a screening with percutaneous nerve evaluation, in which a temporary wired probe electrode is inserted into the S3 foramen. Patients who show a 50% or greater improvement in one or more urine voiding parameters after 3-7 days of electrode stimulation are offered a permanent implantable system. The permanent system is then implanted as follows in existing systems. A midline sacral incision is made, the paravertebral muscles are separated, and a wired lead with a connector at the proximal end is placed in the S3 sacral foramen. Another incision is made over the upper buttock, creating a pocket in which the implantable pulse generator (IPG) is placed. The lead and the IPG are connected with extensions, the incisions are closed, and after a week, the stimulator is programmed for therapeutic use. The procedure can be expensive, and problems arise with many patients, including change in bowel function, infection, pain at implant sites, and/or unpleasant stimulation or sensation.

Implementations disclosed herein may provide for an implantable wireless device that fully contains the electronics necessary to capture and rectify the energy received from outside the body. The implantable wireless device may be remotely powered from outside the body. This remote powering feature may avoid the invasive and expensive portions of the implantation procedure; namely, the incision in the upper buttock for the IPG pocket, as well as any tunneling to connect the controller to the lead. In addition, this remote powering feature may allow for a significantly smaller implantable wireless device, thereby reducing the invasiveness of the procedure and increasing the options for percutaneous delivery of the implantable wireless device directly to the targeted tissue location through the foramen with a spinal needle.

Some implementations relate to the use of a implantable wireless device to medical disorders, such as urological disorders. The urological disorders may include one or more of the following disorders: overactive bladder, urge incontinence, stress incontinence, pelvic pain, bladder pain, bladder inflammation, vesico-urethral dysfunction, genito-urinary disorders, fecal incontinence, urge frequency, urinary pain, erectile/sexual disorders, non-obstructive urinary retention and interstitial cystitis/painful bladder syndrome.

Some implementations may include a system that includes (i) an implantable wireless device containing one or more electrodes adapted for stimulation of the sacral plexus, (ii) passive circuitry, and (iii) at least one antenna for receiving an input signal (as described above) via a manner that is non-inductive. In addition, the system may include an external controller comprising electronic circuitry, a power source and a transmitting antenna for transmitting the input signal to the at least one antenna on the implantable wireless device through radiative electric coupling. A surgical procedure may be conducted by a physician to embed the implantable wireless device into the body of a patient suffering from a urinary disorder. During the surgical procedure, the implantable lead is advanced or delivered subcutaneously and positioned such that the electrodes are implanted on the foramen of, for example, the sacral nerve of the patient. The external controller may be loaded with several predetermined programs to provide control of pulse amplitude, pulse width, frequency, ON time and OFF time of electrical pulses applied by the electrodes on the implantable wireless device. The physician and/or patient may determine the particular program for therapy for effective relief of the urological disorder.

Once the program is determined, the external controller may send an input signal via a radio frequency carrier signal to the antenna within the implantable wireless device and the antenna and internal circuitry on the implantable wireless device may then convert this input signal to electrical pulses. The electrical pulses may be applied to the electrodes within the wireless device to modulate the nerves of the sacral plexus. Sacral nerve stimulation may induce reflex mediated inhibitory effects on the detrusor through afferent and/or efferent stimulation of the sacral nerves. The sensory input traveling through the pudendal nerve can inhibit detrusor activity in the patient.

FIG. 1 illustrates an example of an implantable wireless device 100 for stimulating nerves, such as the sacral nerve. The implantable wireless device 100 includes distal end 102, a device body 114, and proximal end 116.

The distal end 112 includes a rounded tip. The distal end 112 of wireless device 100 may include a non-conductive tip that is rounded with a length of between about 0.5 mm and about 1.0 mm, with a smooth finish for navigating the device through tissue.

The wireless device 100 includes electrodes 102 and houses electronic circuitry 104. Electrodes 102 may be coupled to electronic circuitry 104 by wiring 106. The wireless device 102 may include an electrode mounted on the distal tip. In some implementations, the wireless device may have between one and twenty-four cylindrical electrodes 102 located at distal end 112 with a diameter between about 0.1 mm and about 0.8 mm for stimulation applications. The diameters and other sizes may, of course, vary from one target treatment to another target treatment. The electrodes 102 may have a longitudinal length of between about 0.25 mm and about 6.0 mm from the distal end 112 toward the proximal end 116. The spacing between the electrode contacts may be between about 0.25 mm and about 6.0 mm. The total electrode surface area of the wireless device body may be between about 0.06 mm$^2$ and about 250.0 mm$^2$.

The various wireless devices described herein, including device 100, may include, for example, anywhere from one to twenty-four electrodes 102, any of which can be designated by a programmer user as either a cathode or an anode. For example, electrodes 102 can include multiple cathodes coupled to the targeted tissue as well as at least one anode. The electrode array can receive electrical stimulation pulses ranging from about 0 to about 10 V peak amplitude at a pulse width up to about 1 millisecond. Such stimulation pulses may be from a single receiver element within the lead body. The polarity of the electrodes can produce various volume conduction distributions from the cathodes to the anodes to inhibit or excite surrounding excitable tissue, which may include A-δ and/or primary or secondary c-fiber afferents. To reduce electrode impedance, the electrodes may be made of a conductive, corrosion resistant, biocompatible material such as, for example, platinum, platinum-iridium, gallium-nitride, titanium-nitride, or iridium-oxide.

The electrodes may include circumferential electrodes in addition to an electrode on the distal end 102. Circumferential electrodes may be placed in parallel. The stimulating electrodes may be made of platinum, platinum/iridium alloy, platinum/iridium coated with titanium nitride or other suitable materials. The conductor connecting the terminal of the electrodes is typically made of an alloy of nickel-cobalt. Electrodes according to some implementations may include spiral electrodes, cuff electrodes, steroid eluting electrodes, wrap-around electrodes, linear electrodes, hydrogel electrodes and the like.

The wireless device 100 may receive RF energy from an external source non-inductively and without a wire. Circuitry 104 may process the received RF energy to obtain electrical energy to power the wireless device 100 and to provide electrical pulses for modulating an excitable tissue.

In particular, electronic circuitry 104 of wireless device 100 may convert an input signal received at the one or more antennas into an electrical energy and electrical pulses. In some implementations, extension tubing can provide an enclosure that houses, for example, flex circuitry. The circuitry may be placed in-between the circumferential electrodes or away from the circumferential electrodes. In some embodiments, the electronic circuitry 104 may include one or a plurality of diodes that function to rectify the wireless signal, such as a sinusoidal signal, picked up by the non-inductive antenna(s). The diodes have a low threshold voltage to maximize the energy used for creating waveforms and power. Additionally, electronic circuitry 104 may include a charge balancing microelectronic component to reduce or prevent corrosion as well as a current limiter.

In certain implementations, the electronic circuitry 104 may include one or more non-inductive antennas, a rectifier, a charge balancer, a current limiter, a controller, and a device interface. In brief, the rectifier functions to rectify the signal received by the one or more non-inductive antennas. The rectified signal may provide power to electrodes 102. The rectified signal may also be fed to a charge balance component that is configured to create one or more electrical pulses such that the one or more electrical pulses result in a substantially zero net charge (that is, the pulses are charge balanced). The charge balanced pulses are passed through the current limiter to the electrode interface, which applies the electrical pulses to electrodes 102.

In some implementations, an internal dipole (or other) antenna configuration(s) may be used in the wireless device 100 to receive RF power through electrical radiative coupling. This coupling can allow such device to produce electrical currents capable of stimulating nerve bundles without a physical connection to an implantable pulse generator (IPG) or use of an inductive coil. In some implementations, between two to eight tissue-exposed-ring-antenna coupling contacts may be proximal to the electrodes. The tissue-exposed-ring-antenna coupling contacts may have a longitudinal length of between about 0.25 mm and about 6.0 mm from the distal end 112 toward the proximal end 116. The spacing between the tissue-exposed ring antenna coupling contacts may be between about 5 mm and about 80 mm. In certain implementations, tissue-exposed-small-antenna coupling contacts with a diameter between about 0.2 mm and about 0.6 mm may be used in lieu of the tissue-exposed-ring-antenna coupling contacts.

In some implementations, at least one of the antennas can be constructed as a conductive trace feature contained on one of the circuits. In other implementations, at least one of the antennas can be fabricated as a conductive wire connected to one of the circuits. In various implementations, the implantable wireless device 100 my employ non-inductive, for example, dipole or other antenna configuration(s), to receive RF power through electrical radiative coupling.

A telemetry signal may be transmitted by the implantable wireless device 100 to deliver information to an external controller. The telemetry signal may be sent by modulation of a carrier signal. The telemetry signal does not interfere with the input received to power the implantable wireless device. In one example, the telemetry signal and powering signal are combined into one signal, where the RF telemetry signal is used to modulate the RF powering signal, and thus the implanted wireless device is powered directly by the received telemetry signal; separate electronic subsystems harness the power contained in the signal and interpret the data content of the signal. In other embodiments, the telemetry output rate is at least 8 kilobits per second.

In other implementations, a RF pulse generator system, located externally to the implanted wireless device 100, may store parameters defining the excitation pulses to be applied at electrodes of the implanted wireless device 104, which are transmitted via the second antenna.

For context, neural stimulating devices may utilize a battery-powered or charge-storage component. Such devices are no longer functional once the battery cannot be recharged or charge cannot be stored. Consequently, for an implanted device, a patient would need to undergo a subsequent surgical procedure to obtain a functional replacement device or frequently recharge the device.

In contrast, some implementations disclosed herein do not rely upon battery power or charge storage for operation. In some configurations, the implantable wireless device can receive electrical power from radiated RF energy non-inductively and without a wired connection. As a result, the life of an implanted wireless device may no longer be limited by the life of the battery or ability to store charge.

Further, the electrical radiative coupling mechanism (for example, a dipole antenna) can be utilized to improve the form factor of the implanted wireless device and allow for miniature diameters. Electrical radiative coupling at a higher carrier frequency may also allow for the transmission and reception of energy at greater depths with less degradation in efficiency than inductive coil techniques. This electrical radiative coupling can provide an advantage over devices that employ inductive coupling where the efficiency of such implants may be highly dependent on the distance separating the external transmitter coil and the implanted receiver coil.

Accordingly, some implementations disclosed herein do not include inductive loops to receive RF energies in a wireless manner. Instead, some implementations disclosed herein use electric radiative coupling to receive RF energies. Such implementations facilitate a smaller form factor for a fully functional implantable electrical stimulation or recording device. The improved form factor may result in a less invasive surgical procedure for placement of the device. The improved form factor may also decrease scarring the amount of bodily tissue in contact with the implanted device is reduced.

FIGS. 2A-2D depict implantable devices with various types of suturing features. FIG. 2A shows an implantable wireless device 210 with suturing feature as flat wing feature 202. The flat wing feature 202 is similar to suturing feature 108. The flat wing feature 202 includes pass through holes through which a physician may anchor the respective wireless device to surrounding tissue. A wireless device 210 includes electrodes 102, as discussed above. Other suturing features, including a barb feature 204, a pass-through feature 206, and a knob feature 208 are present on implantable wireless devices 220, 230, and 240, as shown in FIGS. 2B-2D, respectively.

Figure 3A:
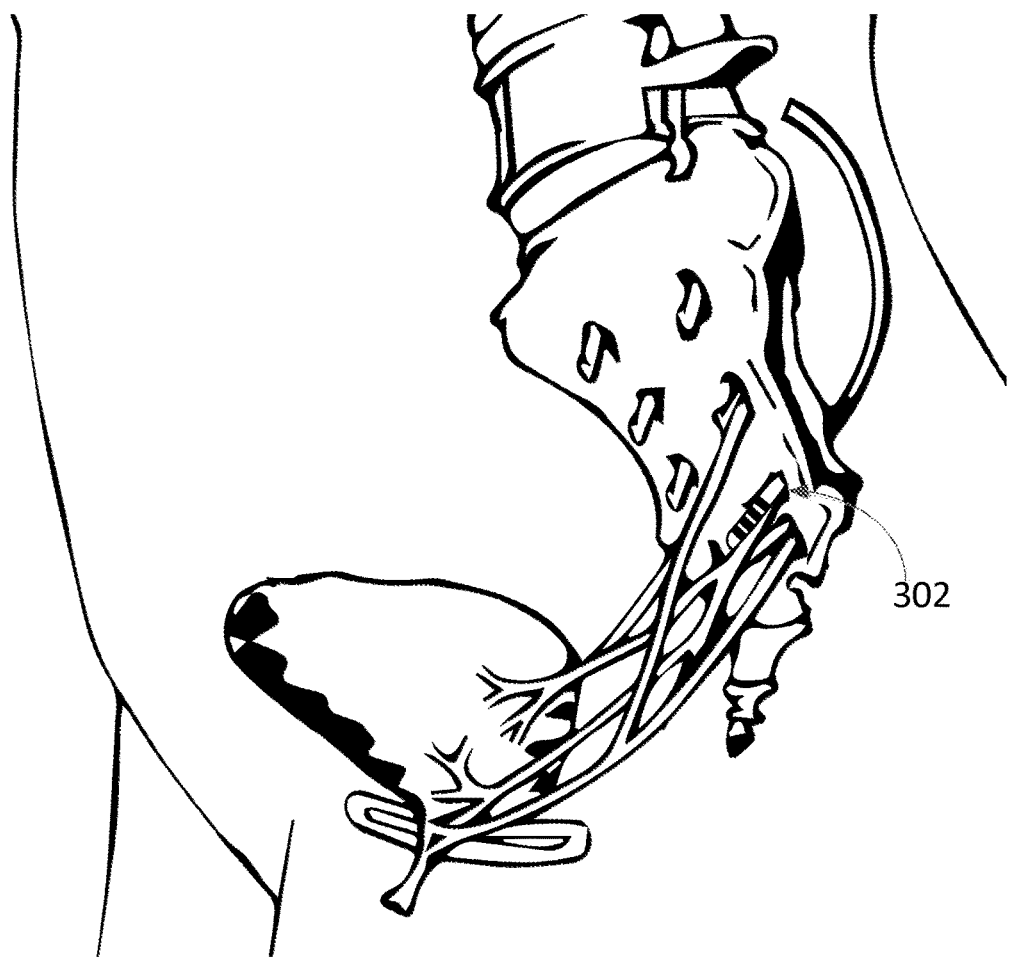
FIGS. 3A and 3B show a diagram of the sagittal section of the female pelvis, showing the relationship between various anatomic structures and a lead.
Figure 3B:
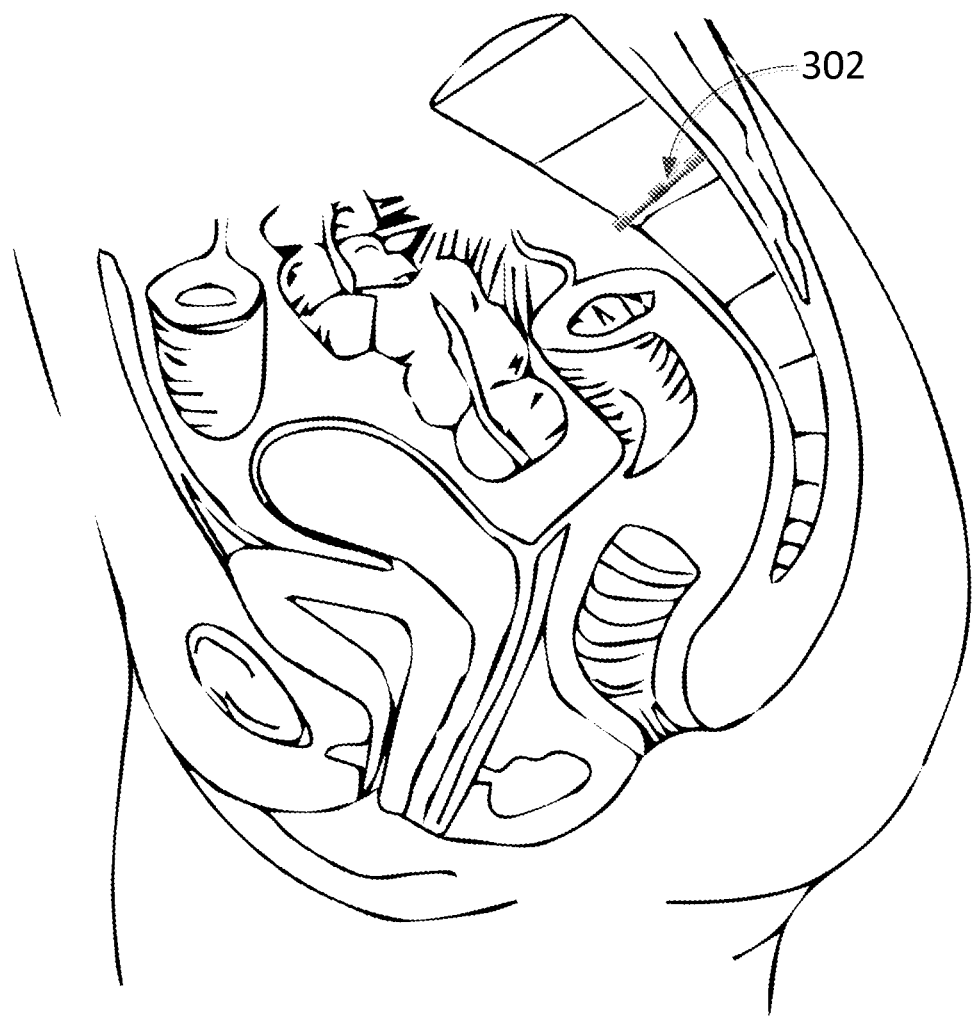

Systems and methods disclosed herein may also find applications in stimulating nerves or nerve bundles in the sacral or pelvic region to treat erectile/sexual dysfunction, prostatitis, prostatitis pain and chronic pelvic pain. FIGS. 3A and 3B show a diagram of the sagittal section of the pelvis region. An implantable wireless device 302 may be placed into the sacral or pelvic regions. In both diagrams, the implantable wireless device 302 is positioned adjacent to or near the sacral nerve. Once the implantable wireless device 302 is implanted, an external controller (as described above, and below) sends the input signal to the internal antennas contained within the implanted wireless device. The input signal may include the electrical power to drive the wireless device, as well as the excitation pulses carried via a higher frequency carrier signal. The electrical pulses may be applied through the electrodes on the wireless device to the targeted nerve. The application of excitation pulses may modulate the nerves and create action potentials in the nerves to treat, for example, the patient's pelvic pain, erectile dysfunction, or other forms of urological disorder.

Figure 4:
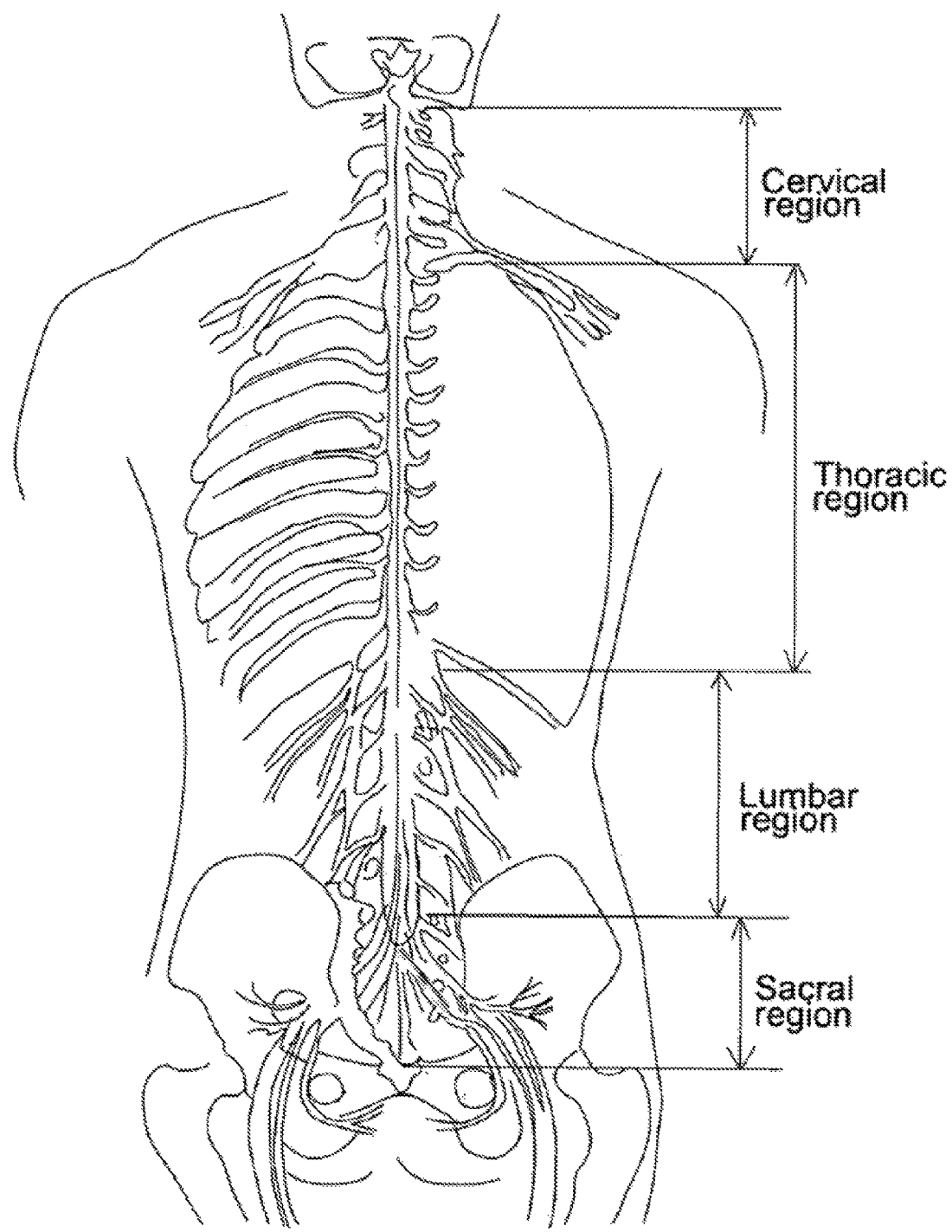
FIG. 4 is a diagram showing schematic relationships of spinal nerves and the sacral region.

FIG. 4 is a diagram showing schematic relationships of spinal nerves and the sacral region. The implantable wireless device may be placed adjacent to or near any spinal nerves or a sacral nerve in the sacral region.

Figure 5:
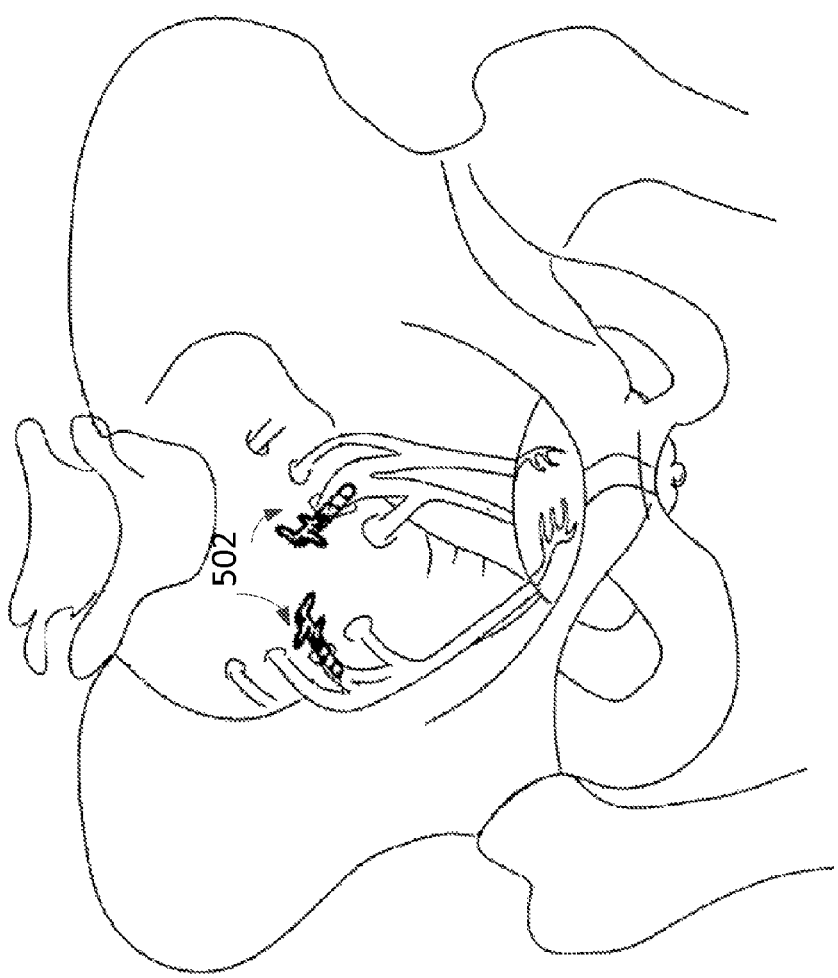
FIG. 5 is a schematic diagram of the sacral region showing placement of the implanted wireless device in the sacral foramen.

FIG. 5 is a schematic diagram of the sacral region showing electrodes in the sacral foramen, and placement of the wireless device. In one example, stimulation is provided to the cavernous nerve or pudendal nerve to treat erectile dysfunction. In this example, an incision is made for exposing the cavernous or pudendal nerves and the distal portion of the wireless device is placed in the tissue such that the electrodes are in contact with the target nerves. In another example, stimulation is provided to the pudendal nerve, the prostatic plexus or the sacral splanchnic nerve to treat prostatitis or chronic pelvic pain. Similar to the above example, an implantable wireless device is positioned adjacent to or near one or more of the pudendal nerve or its branches.

Figure 6A:
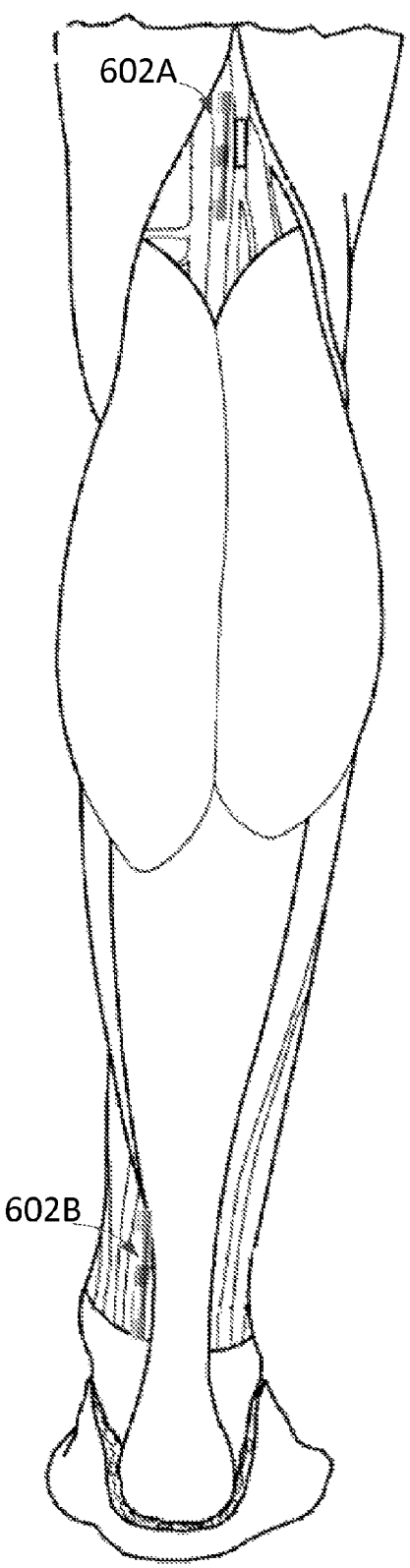
FIGS. 6A and 6B illustrate examples of locations for implantation of a wireless device for stimulating the tibial nerve.
Figure 6B:
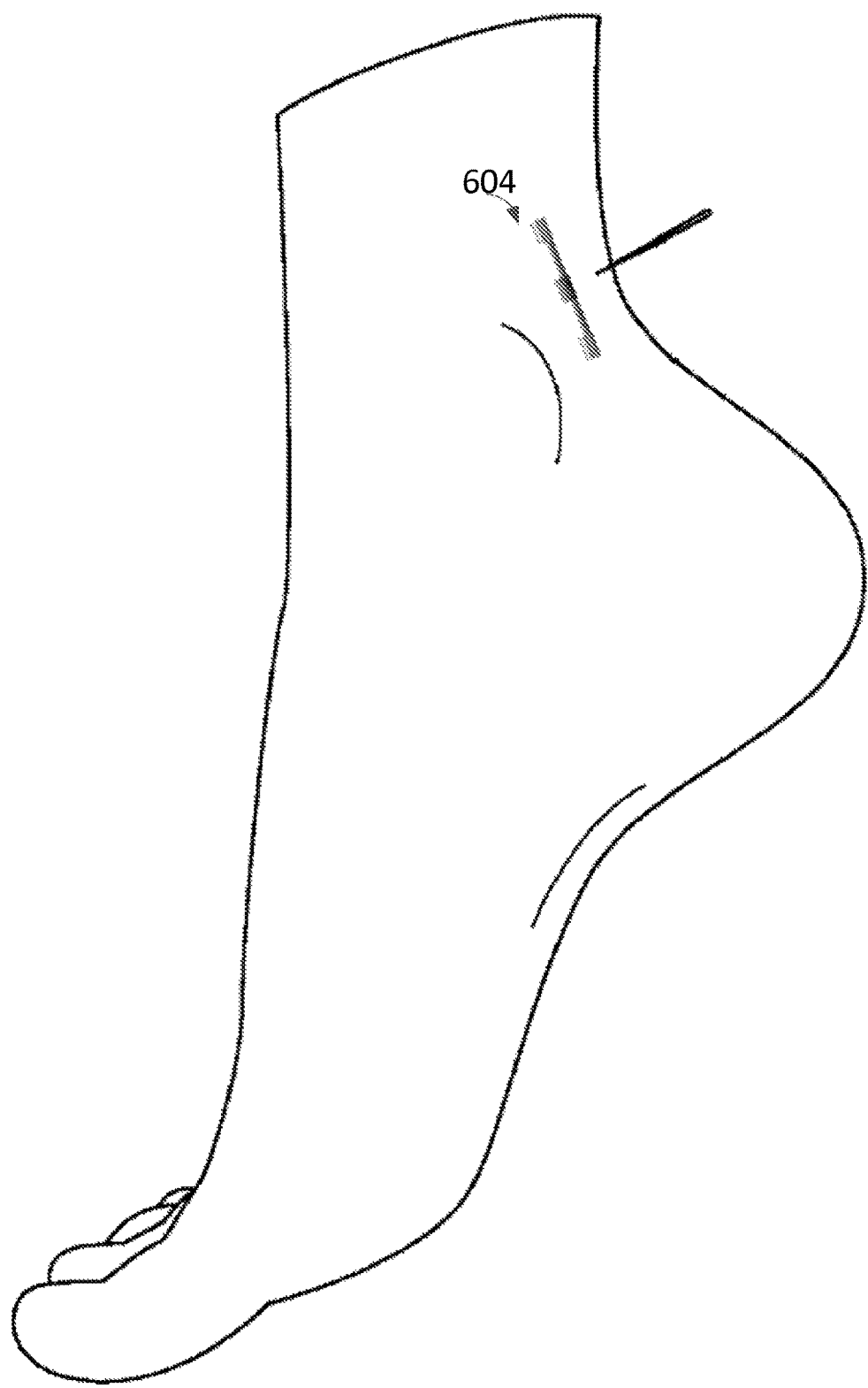

Now referring to FIGS. 6A to 6B, systems, devices and methods for stimulating the tibial nerve are described. Tibial nerve stimulation may treat overactive bladder. Rather than requiring an incision and placement of electrodes in the sacrum, tibial nerve stimulation stimulates sacral nerve roots, but at a location much closer to the surface of the skin, e.g., typically at the posterior tibial nerve slightly above the ankle. The rationale is that the tibial nerve, a branch of the sciatic nerve, is derived from spinal nerves L4 through S3, which are involved in the control of the bladder.

Tibial nerve stimulation can be performed with a percutaneous electrode approach referred to as percutaneous nerve stimulation (PTNS), wherein an electrode needle is inserted to the target area and then removed after the stimulation session is completed. In an example percutaneous approach, a sensitive pressure point is identified, for example, approximately three finger breadths cephalad from the medial malleolus and about one finger breadth posterior from the edge of the tibia. A needle is inserted through the skin approximately 3 to 4 cm posterior to the tibia. The angle of the needle is 60 degrees cephalad from a perpendicular line along the length of the tibia. A ground pad is placed over the medial aspect of the calcaneus. A stimulator is then connected to the needle and the ground pad. A current 0.5-9 mA at 20 Hz provides stimulation. Each treatment session lasts 30 minutes, and the sessions are conducted weekly.

An implantable approach can be used for tibial nerve stimulation. The implantable approach may be similar to PTNS except that the stimulator device is implanted adjacent to or near the target area of the tibial nerve. This approach may not require the patient to return to the physician's office for each treatment session. Once the device is implanted, the patient may complete treatment sessions on his own at home. Typically, the pulse generator and power supply are implanted in another location of the body and connected to the implanted lead with long extension cabling that is tunneled from the target nerve location to the location of the pocket for the implantable pulse generator.

Using the wireless devices described in this application alleviate the need to implant the pulse generator power supply and connectors. In particular, some implementations employ a system that includes an implantable wireless device containing one or more electrodes adapted for stimulation of the tibial nerve, passive circuitry and an antenna for receiving an input signal (as described above, and below). In addition, the system may include an external controller comprising electronic circuitry, a power source and a transmitting antenna (as described above and below). During the surgical procedure, the implantable wireless device is advanced or delivered subcutaneously and positioned such that the electrodes are implanted adjacent to or near a suitable location on the tibial nerve.

Once implanted, the external controller sends an input signal via a radio frequency (RF) input signal (as described above and below) to the antenna within the implantable lead and the antenna and internal circuitry then convert this input signal to electrical pulses. The coupling between antennas on the controller and antennas within the implantable wireless device may include a radioactive electric coupling, rather than inductive coupling. The electrical pulses are applied to the electrodes within the wireless device to modulate the nerves of the tibial nerve. Thus, there is no requirement to implant the pulse generator and power supply within the patient. The patient may activate the external controller at his/her discretion at home to stimulate the nerve(s) and complete treatment sessions.

Exemplary wireless devices for use in the systems and methods described herein are described below in reference to FIGS. 7-17. The depths of these nerves range between about 2.0 mm and 1.0 cm, but are accessible and treatable through minimally invasive operations and injections. The wireless devices can contain between 1 and 8 electrodes, with a diameter from between 0.1 mm to 1.4 mm. The electrodes may have a longitudinal length of between about 0.25 mm and about 6.0 mm from the distal tip toward the proximal tip. The spacing between the electrode contacts may be between about 0.25 mm and about 6.0 mm. The total electrode surface area of the wireless device body may be between about 0.06 mm$^2$ and about 250.0 mm$^2$. A patient may have eight or more wireless devices implanted while still being able to receive individual power and instruction sets and stimulate tissue.

The various devices described herein may include anywhere from two to sixteen electrodes, any of which can be designated by the programmer as either a cathode or an anode. For example, electrodes can include multiple cathodes coupled to the targeted tissue as well as at least one anode. The electrode array can receive electrical stimulation waveform pulses ranging from 0 to 10 V peak amplitude at a pulse width reaching up to a maximum of 1 millisecond. The polarity of the electrodes can produce various volume conduction distributions from the cathodes to the anodes to inhibit or excite surrounding nerve tissue, which may include A-δ and/or primary or secondary c-fiber afferents. To minimize electrode impedance, the electrodes may be made of a conductive, corrosion resistant, biocompatible material such as, for example, platinum, platinum-iridium, gallium-nitride, titanium-nitride, or iridium-oxide.

Excluding the electrodes, which are coupled to the surrounding tissue, the remaining portions of the wireless device embodiments described herein may be insulated from surrounding body tissue partially or totally by an external coating layer of biocompatible dielectric material with a low dielectric constant. Materials with rigidity similar to that of tissue can be used to reduce the risk of migration and the development of fibrous scar tissue. Such fibrous scar tissue can increase electrode-tissue impedance. If the electrode-tissue impedance can be kept low, less energy may be consumed to achieve stimulation of the targeted tissues.

The antenna can be, for example, a dipole antenna. Some embodiments may have only one dipole antenna, other embodiments may have multiple antennas of any given length. For example, without limitation, some embodiments may have between two and ten dipole antennas, while other embodiments can have more than ten dipole antennas or more than twenty dipole antennas. In some embodiments, a dipole antenna can range from about 100 microns to about 10 cm in length. In other embodiments, an antenna can consist of any linear dipole configuration ranging from about 20 microns to about 3 mm in thickness. The antenna may also be a folded dipole antenna instead of a straight dipole antenna.

The antenna may be configured to receive RF energy from exterior antennas. RF wave propagation energy is divided into two regions, the radiative region and the reactive region. The radiative region is within $2D^2/\lambda$ and the radiated power varies with distance from the antenna. For a short dipole antenna, the reactive component is approximately $\lambda/2\pi$. The induced field for antennas placed in biological tissue is a function of body geometry, tissue properties, and the exposure conditions. The efficiency of the RF waveform inside a lossy media, such as body tissue, is attenuated by the tissue as it propagates. To increase the power efficiency of a small antenna in lossy matter, the dipole antenna configuration can be optimized at high frequencies to minimize losses, such as, for example, from about 800 MHz to 5.8 GHz or greater. A more complete description of exemplary antennas can be found in the commonly assigned co-pending PCT applications referenced above.

In certain implementations, the antenna coupling contacts have a longitudinal length between about 0.25 mm and about 6.0 mm from the distal tip toward the proximal tip and a diameter of between about 0.1 mm to about 1.4 mm. The spacing between the antenna coupling contacts may be between about 5 mm and about 80 mm. The antenna coupling contracts may improve the efficiency of the radiative coupling between internal antenna and the antenna(s) located externally to the body. The antenna coupling contacts may be made of noncorrosive metals, such as, for example, platinum, platinum-iridium, gallium-nitride, titanium-nitride, or iridium-oxide.

Antenna coupling contacts may be connected by conducting wires to the antenna(s) and the waveform conditioning circuit. The waveform conditioning circuitry may include, for example, electronic components such as diodes, resistors and capacitors. The waveform conditioning circuitry uses the incoming energy to provide a stimulation waveform to the electrodes for excitation of nerve tissue. In some embodiments, frequencies from about 300 MHz to about 5.8 GHz, preferably from about 800 MHz to about 2.5 GHz, may be received by the implanted antenna. The stimulating waveform released into the tissue from the electrodes is rectified to provide waveforms at lower frequencies, e.g., at typically from about 5 Hz to about 1000 Hz, but can be as high as 10,000 Hz or more.

The waveform conditioning circuitry may be configured to rectify the waveform signal received by the implanted antenna. The waveform conditioning circuitry may also have charge balance microelectronics to prevent the corrosion of the electrodes. To minimize reflection of the energy back from the electrodes into the circuitry, the waveform-conditioning circuitry may include isolation circuits to block high frequency signals.

Figure 7:
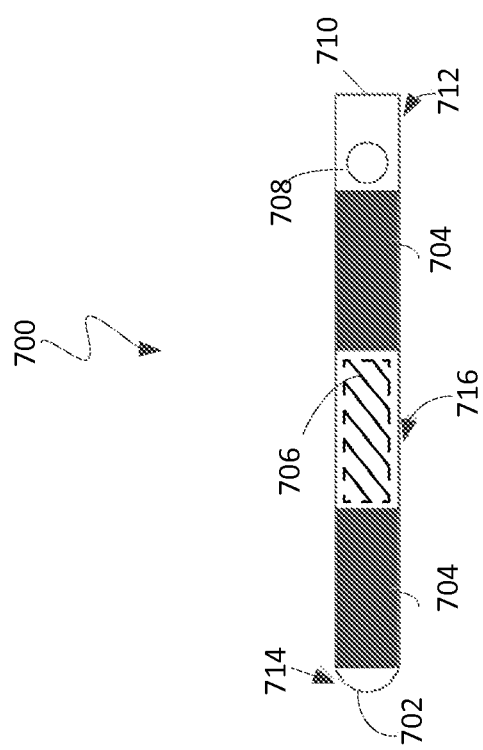
FIG. 7 illustrates an example of a miniature implantable device including wireless power receiving electronics.

FIG. 7 illustrates an example miniature implantable device 700. The implantable device 100 includes a body 716 with a distal end 714 and a proximal end 712.

The distal end 714 includes a rounded tip 702. The distal end 714 of the miniature wireless device body 716 may include a non-conductive tip 702 that is rounded with a length of between about 0.5 mm and about 1.0 mm, with a smooth finish for navigating the device through tissue.

The device body 706 includes electrodes 704 and houses electronic circuitry 706. In some implementations, the miniature implantable device may have between one and twenty-four cylindrical electrodes 704 on its distal end 714 with a diameter between about 0.1 mm and about 0.8 mm for stimulation applications. The diameters and other sizes may, of course, vary from one target treatment to another target treatment. The electrodes 704 may have a longitudinal length of between about 0.25 mm and about 6.0 mm from the distal end 714 toward the proximal end 712. The spacing between the electrode contacts may be between about 0.25 mm and about 6.0 mm. The total electrode surface area of the cylindrical wireless lead body may be between about 0.06 mm$^2$ and about 250.0 mm$^2$.

The proximal end 712 includes a suturing feature 708 and a mating feature 710. The suturing feature 708 is a passage through the proximal end with a central axis that is parallel to a longitudinal axis of the device body 706. Suturing feature 708 may allow a clinician to suture and anchor implantable device 700 during an implantation procedure. For instance, suture can be passed through the passage of suturing feature 708 and tied to tissue. In some cases, the implantable device 700 can be sutured to the surrounding tissue. Suturing the implantable device may reduce mobility and improve stability of the implanted device.

Mating feature 710 may allow the device 700 to be mechanically mated with a stylet, as disclosed herein. In one configuration, mating feature 710 is a concave indentation that extends along a longitudinal axis of the device body 706 from the proximal end 712. The concave indentation mates with a corresponding feature on a placement stylet or suction stylet. The concave stylet-mating feature on the proximal end 710 of implantable device 700 can have, for example, a length of between about 0.1 mm and 1.0 mm. In other configurations, the stylet-mating feature 710 may be semi-spherical or asymmetrical in shape for improved steerability of the device during implantation.

The various devices described herein, including device 700, may include, for example, anywhere from one to twenty-four electrodes 704, any of which can be designated by a programmer user as either a cathode or an anode. For example, electrodes 704 can include multiple cathodes coupled to the targeted tissue as well as at least one anode. The electrode array can receive electrical stimulation pulses ranging from about 0 to about 10 V peak amplitude at a pulse width up to about 1 millisecond. Such stimulation pulses may be from a single receiver element within the device body. The polarity of the electrodes can produce various volume conduction distributions from the cathodes to the anodes to inhibit or excite surrounding excitable tissue, which may include A-δ and/or primary or secondary c-fiber afferents. To reduce electrode impedance, the electrodes may be made of a conductive, corrosion resistant, biocompatible material such as, for example, platinum, platinum-iridium, gallium-nitride, titanium-nitride, or iridium-oxide.

The miniature implantable device 700 may be 0.8 mm diameter or smaller. Miniature implantable device 700 may receive microwave or RF energy from an external source non-inductively and without a wire. The miniature implantable 700 device may contain the circuitry necessary to receive the pulse instructions from a source external to the body.

In particular, electronic circuitry 706 of the miniature implantable device may convert an input signal received at the one or more antennas into an electrical energy and electrical pulses. In some implementations, extension tubing can provide an enclosure that houses, for example, flex circuitry. In some embodiments, the electronic circuitry 706 may include one or a plurality of diodes that function to rectify the wireless signal, such as a sinusoidal signal, picked up by the non-inductive antenna(s). The diodes have a low threshold voltage to maximize the energy used for creating waveforms and power. Additionally, internal circuitry 706 may include a charge balancing microelectronic component to reduce or prevent corrosion as well as a current limiter.

In certain embodiments, the electronic circuitry 706 may include one or more non-inductive antennas, a rectifier, a charge balancer, a current limiter, a controller, and a device interface. In brief, the rectifier functions to rectify the signal received by the one or more non-inductive antennas. The rectified signal may provide power to electrodes 704. The rectified signal may also be fed to a charge balance component that is configured to create one or more electrical pulses such that the one or more electrical pulses result in a substantially zero net charge (that is, the pulses are charge balanced). The charge balanced pulses are passed through the current limiter to the electrode interface, which applies the electrical pulses to electrodes 704.

In some implementations, an internal dipole (or other) antenna configuration(s) may be used in lead 100 to receive RF power through electrical radiative coupling. This coupling mechanism can allow such devices to produce electrical currents capable of stimulating nerve bundles without a physical connection to an implantable pulse generator (IPG) or use of an inductive coil. In some implementations, between two to eight tissue-exposed-ring-antenna coupling contacts may be proximal to the electrodes. The tissue-exposed-ring-antenna coupling contacts may have a longitudinal length of between about 0.25 mm and about 6.0 mm from the distal end 714 toward the proximal end 710. The spacing between the tissue-exposed ring antenna coupling contacts may be between about 5 mm and about 80 mm. In certain implementations, tissue-exposed-small-antenna coupling contacts with a diameter between about 0.2 mm and about 0.6 mm may be used in lieu of the tissue-exposed-ring-antenna coupling contacts.

In some implementations, at least one of the antennas can be constructed as a conductive trace feature contained on one of the circuits. In other implementations, at least one of the antennas can be fabricated as a conductive wire connected to one of the circuits. In various implementations, implantable device 700 my employ non-inductive, for example, dipole or other antenna configuration(s), to receive RF power through electrical radiative coupling.

For context, neural stimulating devices may utilize a battery-powered or charge-storage component. Such devices are no longer functional once the battery cannot be recharged or charge cannot be stored. Consequently, for an implanted device, a patient would need to undergo a subsequent surgical procedure to obtain a functional replacement device.

In contrast, some implementations disclosed herein do not rely upon battery power or charge storage for operation. In some configurations, the implantable device can receive electrical power from radiated RF energy non-inductively and without a wired connection. As a result, the life of an implanted device is no longer limited by the life of the battery or ability to store charge.

Further, the electrical radiative coupling mechanism (for example, a dipole antenna) can be utilized to improve the form factor of the miniature implanted device and allow for miniature diameters. Electrical radiative coupling may also allow for the transmission and reception of energy at greater depths with less degradation in efficiency than inductive coil techniques. This electrical radiative coupling can provide an advantage over devices that employ inductive coupling where the efficiency of such implants may be highly dependent on the distance separating the external transmitter coil and the implanted receiver coil.

Accordingly, some implementations disclosed herein do not include inductive loops to receive RF energies in a wireless manner. Instead, some implementations disclosed herein use electric radiative coupling to receive RF energies. Such implementations facilitate a smaller form factor for a fully functional implantable electrical stimulation or recording device. The improved form factor may result in a less invasive surgical procedure for placement of the device. The improved form factor may also decrease scarring the amount of bodily tissue in contact with the implanted device is reduced.

A telemetry signal may be transmitted by the miniature implantable device 100 to deliver information to an external controller. The telemetry signal may be sent by modulation of a carrier signal. The telemetry signal does not interfere with the input received to power the miniature implantable device. In one example, the telemetry signal and powering signal are combined into one signal, where the RF telemetry signal is used to modulate the RF powering signal, and thus the implanted device is powered directly by the received telemetry signal; separate electronic subsystems harness the power contained in the signal and interpret the data content of the signal. In other embodiments, the telemetry output rate is at least 8 kilobits per second.

In other implementations, a RF pulse generator system, located externally to the miniature implanted device 700, may store parameters defining the excitation pulses to be applied at electrodes 704, which are transmitted via the second antenna.

Figure 8:
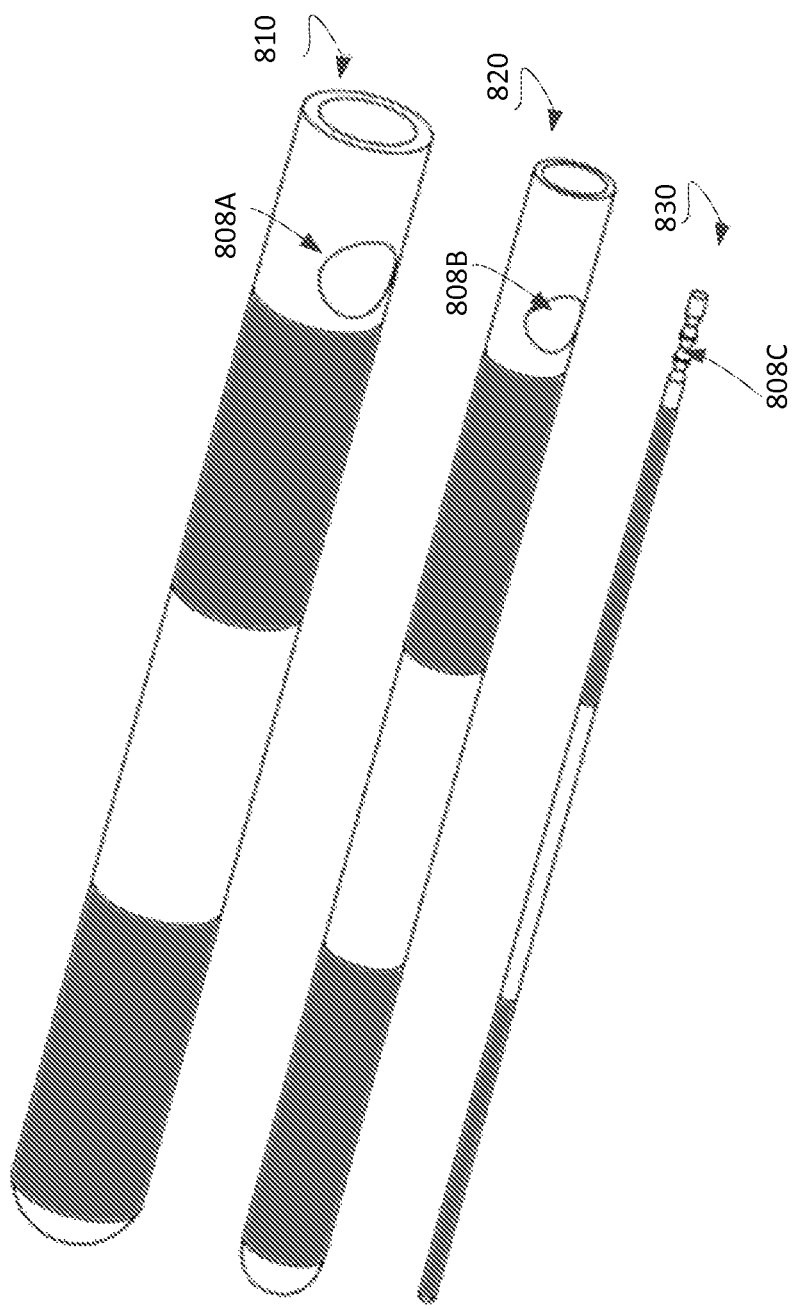
FIG. 8 shows three different sized miniature implantable devices.

FIG. 8 illustrates three examples of miniature implantable devices 800A, 800B, and 800C with various diameters. Miniature implantable device 800A is a miniature implantable device with a diameter of 0.8 mm. Miniature implantable device 800A includes a suturing feature 808A to allow a clinician to suture and anchor implantable miniature implantable device 800A during an implantation procedure. For instance, suture can be passed through the passage of suturing feature 808A and tied to tissue such that the mobility of the implanted device is reduced. As illustrated, implantable device 800A also includes an indentation 810A on the proximal end to allow for mating with a placement stylet during implantation.

Miniature implantable device 800B has a diameter of 0.4 mm and has a suturing feature 808B similar to 808A. Implantable device 800B also includes an indentation 810B on the proximal end to allow for mating with a placement stylet during implantation.

Miniature implantable device 800C has a diameter of 0.1 mm. Miniature implantable device 800C includes a suturing feature 808C in the form of ribs to aid suture in attaching to a surrounding tissue. Implantable device 800C also may include an indentation 810C to allow for mating with a placement stylet during implantation.

Figure 9:
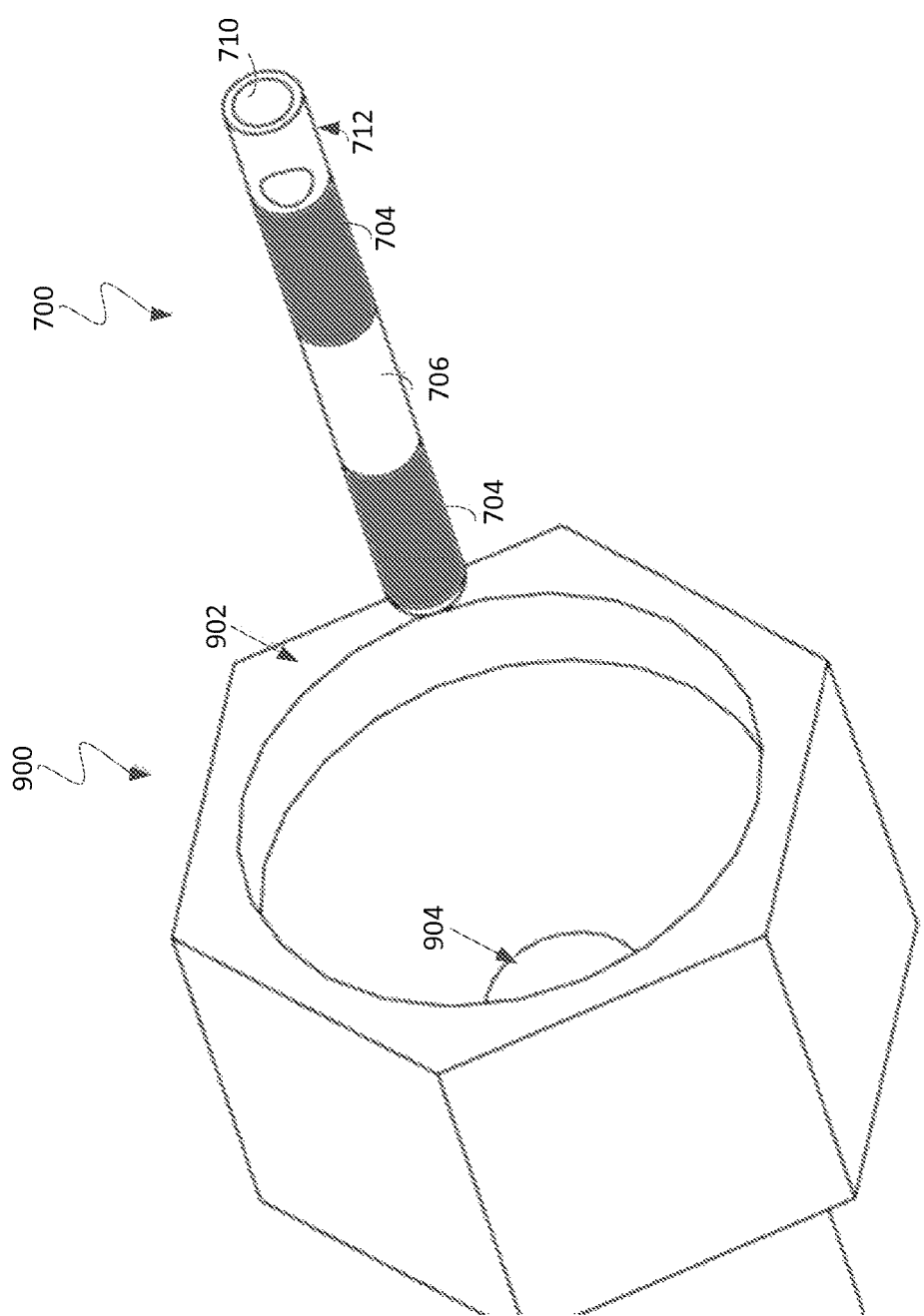
FIG. 9 illustrates a miniature implantable device entering an introducer needle.

FIG. 9 illustrates the miniature wireless device 700 (e.g., a 0.8 mm diameter) entering an 18 gauge needle 900. The distal end (not shown) of miniature implantable device is in position to enter the proximal opening 902 of an 18-gauge needle 900. Miniature implantable device 900 has a diameter small enough to fit into the inner lumen 904 of the needle 900. The illustration may correspond to an implantation of a miniature implantable device with a diameter of 0.8 mm, shown as the implantable device 800A in FIG. 8. Notably, the middle and bottom devices (0.4 mm and 0.1 mm, respectively) shown in FIG. 8 are sized for advancement through introducer needles with even smaller sizes, (e.g., 22 gauge or smaller).

While it is possible to place the device 700 directly into an introducer needle, doing so may not be desirable as the implantable device enclosure may not be as rigid as a guide wire and may not slide easily within the inner lumen of the introducer needle. Yet, a guide wire may not be used because the implantable device may not have a central void through which to mount the guide wire. To improve the ease of placement through an introducer needle, a stylet may be used to provide some rigidity to the miniature device.

Figure 10A:
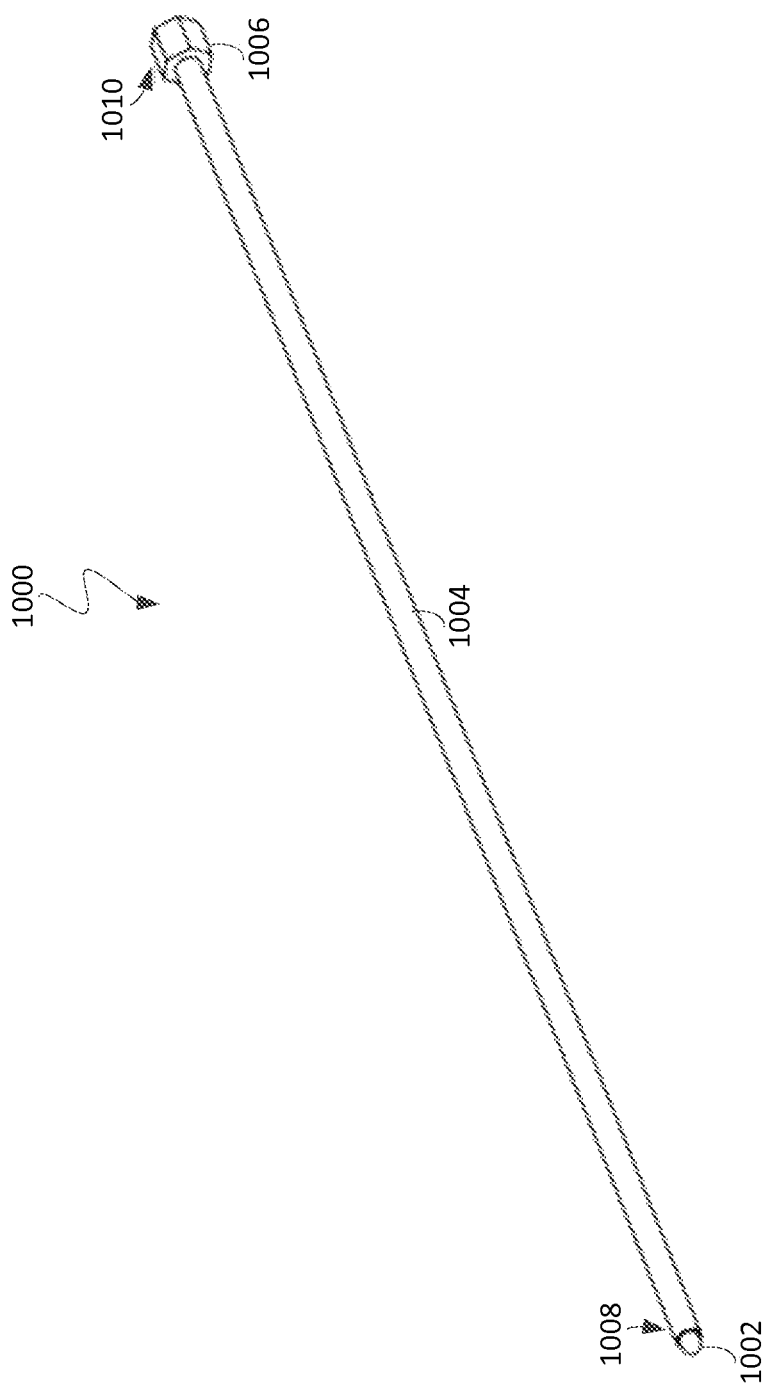
FIG. 10A shows a placement stylet capable of mating with a miniature implantable device.

FIG. 10A shows a placement stylet 1000 capable of mating with a miniature implantable device 700 according to some implementations. Placement stylet 1000 includes a distal end 1008, device body 1004, and proximal end 1010. Distal end 1008 includes a mating feature 1002 to allow the placement stylet 1000 to engage, for example, miniature implantable device 700. The mating feature 1002 is, for example, a convex protrusion that is shaped and sized to mate with the concave indentation 710 of the lead 700. Proximal end 1006 includes handle 1006 for operator to hold placement stylet 1000, for example, during an implantation procedure. Placement stylet 1000 can have a longitudinal length of between about 50 mm and about 177 mm. Placement stylet 1000 can have an outer diameter in the range from between about 0.1 mm and about 0.9 mm. Placement stylet 1000 may be made of a rigid biocompatible material such as stainless steel, titanium, nylon, or polyethylene.

Figure 10B:
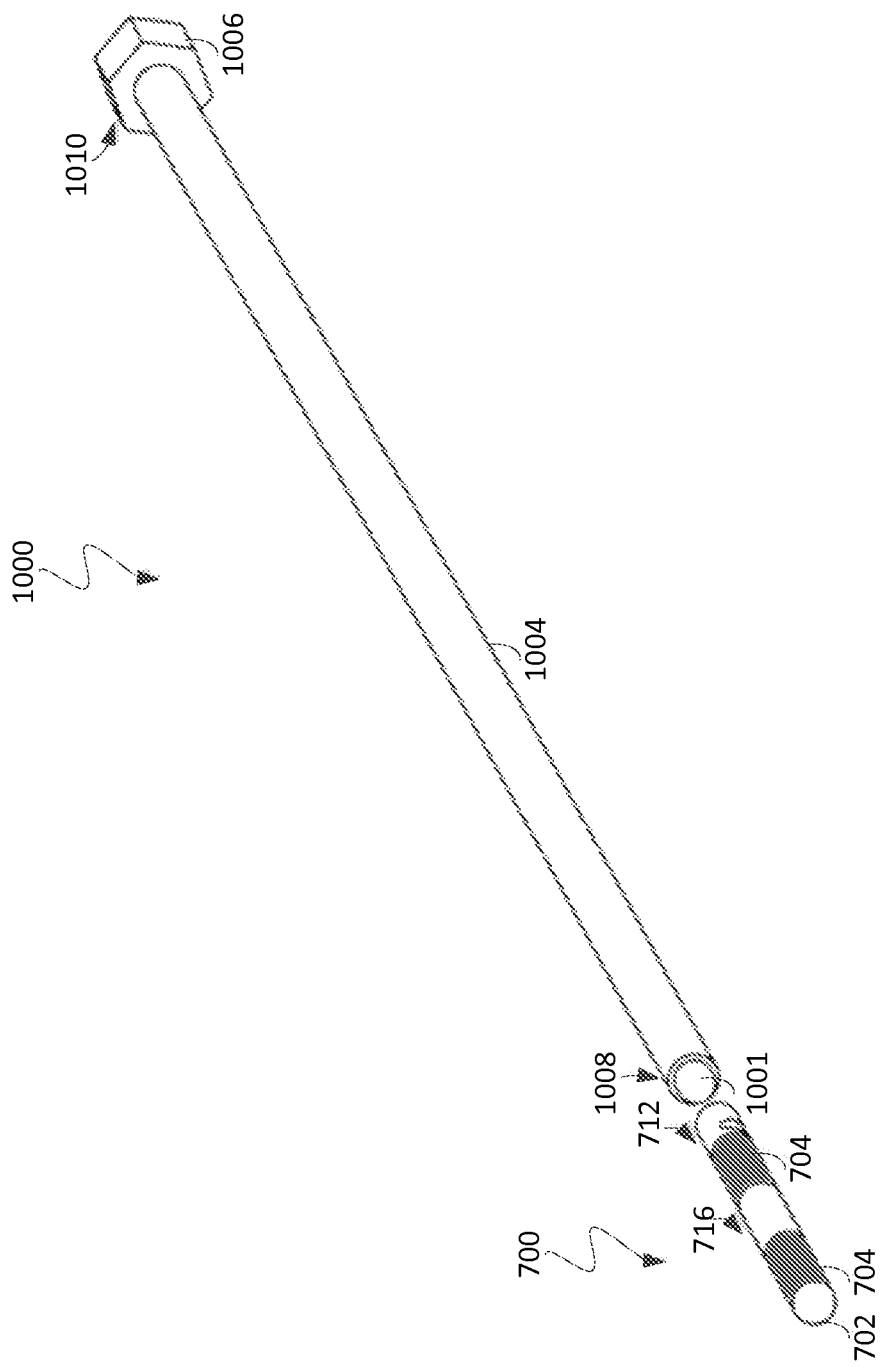
FIG. 10B illustrates a miniature implantable device mated with a placement stylet.

FIG. 10B illustrates a miniature implantable device 700 mated with a placement stylet 1000. A clinician may mate the miniature implantable device 700 onto the placement stylet 1000. The mating feature 1002 on the distal end 1008 of the stylet may mate with mating feature 710 on the proximal end 712 of miniature implantable device 700. Mating feature 1002 on placement stylet 1000 may be semi-spherical in shape, and may provide mechanical gripping for placement stylet 1000 to engage the miniature implantable device 700 during placement. Mating feature 1002 may be complementary in shape to the shape of mating feature 712 on the proximal end 710 of the device 700. In some configurations, mating feature 1002 may be convex in shape. In other configurations, mating feature 1002 may include extruded shapes for mating the stylet 900 to the miniature implantable device 1000 at mating feature 712, which may have a square, hexagon, star, or an asymmetrical shape. Mating feature 1002 may only protrude from the distal end 1008 of placement stylet 1000 from between 0.1 mm and 1.0 mm and may not fill the entirety of the device body 706 (that is, the feature 1002 may only extend partially into device body 706). Mating feature 1002 may have a surface material that allows for increased friction to improve the mate between placement stylet 1000 and the miniature implantable device 700. Example materials may include silicon or polyurethane.

Figure 11A:
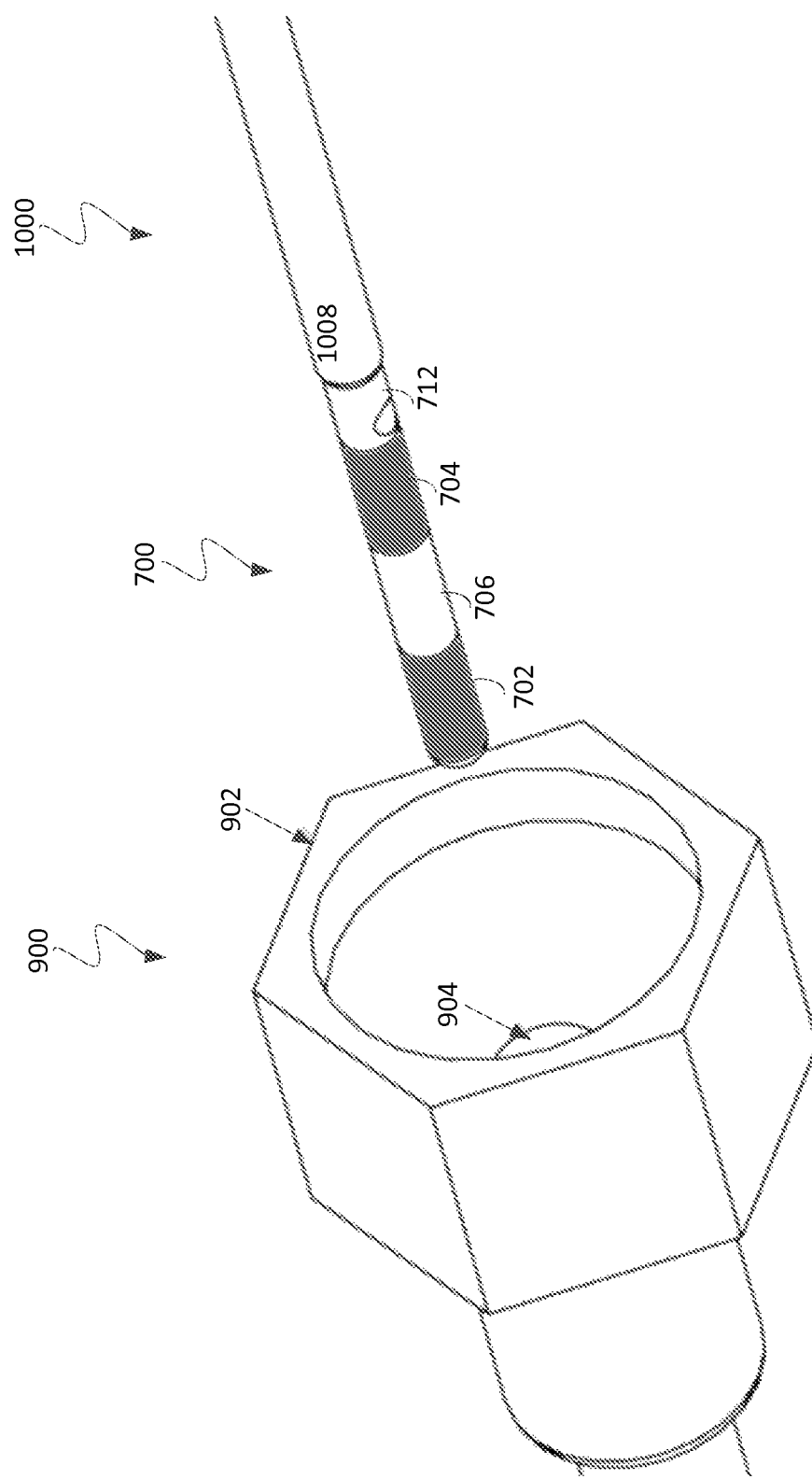
FIG. 11A shows a miniature implantable device mated with a placement stylet entering a proximal opening of an introducer needle.

FIG. 11A illustrates a miniature implantable device 700 mated with a placement stylet 1000 entering a proximal opening 1002 of needle 900. Miniature implantable device 700 includes lead body 716 that includes electrodes 604 and houses electronic circuitry 706. The proximal end 712 of miniature implantable device 700 is now mated with the distal end 1008 of placement stylet 1000. As illustrated, after the miniature implantable device 700 has been mated to placement stylet 1000, the subassembly of the device 700 with the stylet 1000 can now be inserted into an 18 gauge needle 900 or smaller. In particular, the miniature implantable device 700 at the proximal opening 302 of needle 900 is being pushed into position with the placement stylet 1000. In fact, the stylet/miniature device subassembly may now slide freely within the inner lumen 904 of the needle 900. The free sliding motion may aid in the surgical placement of the miniature device 700.

Figure 11B:
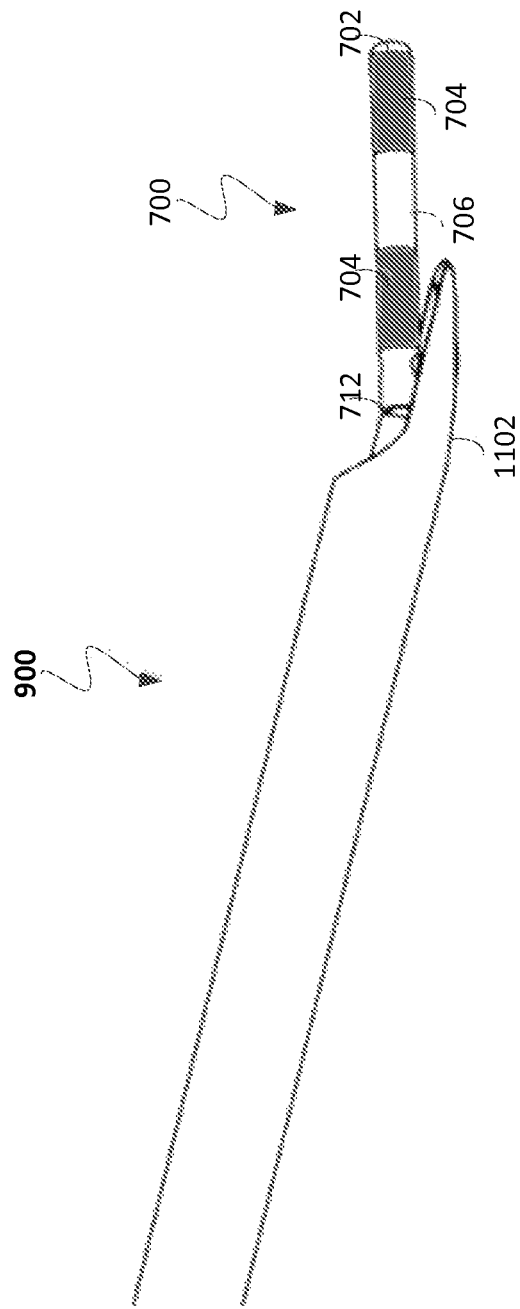
FIGS. 11B and 11C show a miniature implantable device mated with a placement stylet exiting a distal tip of an introducer needle.
Figure 11C:
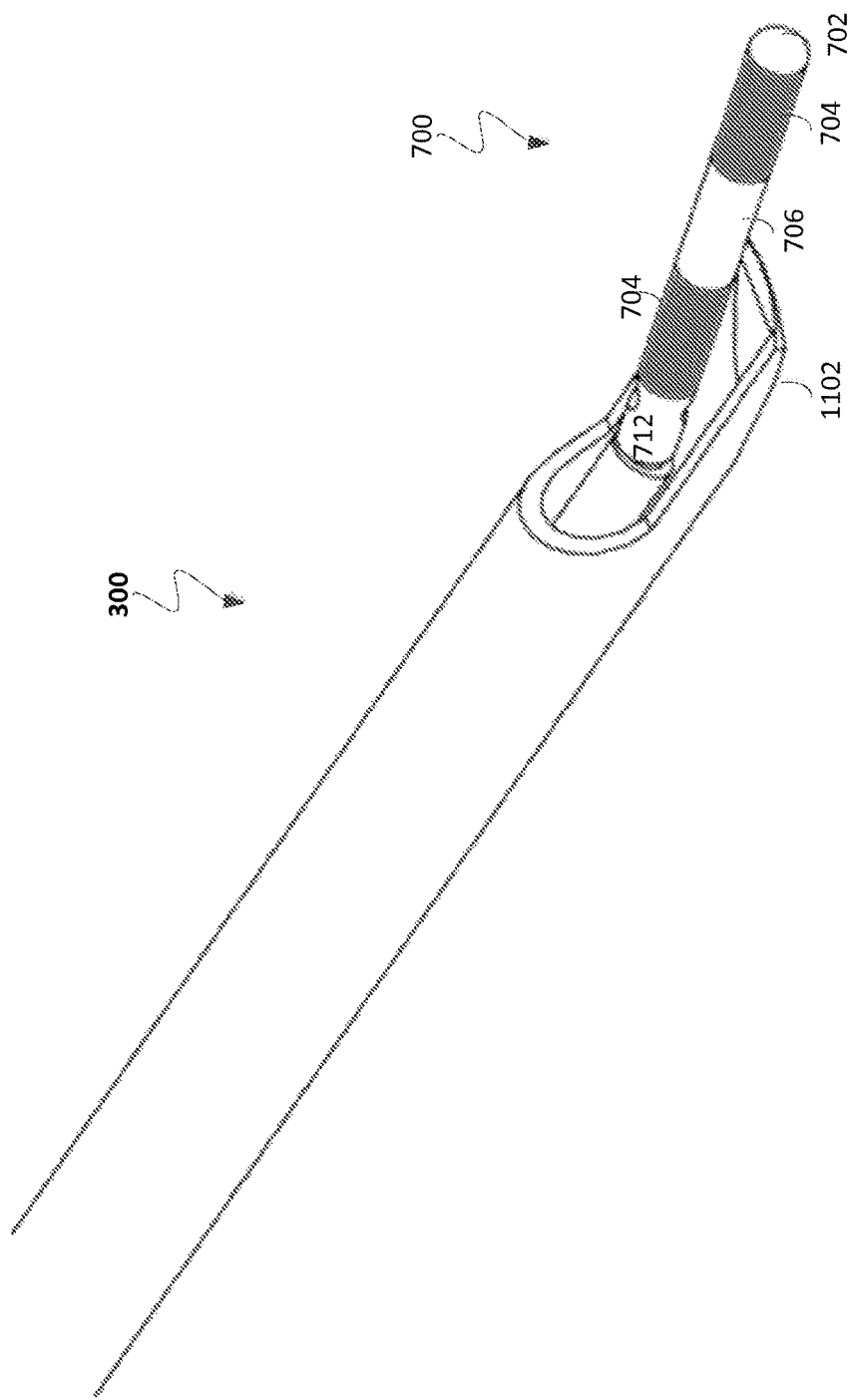

FIGS. 11B and 11C show a miniature implantable device 700 mated with a placement stylet 1000 exiting a distal end 1002 of needle 900. As discussed above, the miniature implantable device 700 may freely traverse the inner lumen 904 of needle 900 with a size of 18 gauge or smaller. Once the traversal is completed, the miniature implantable device 700 may exit the needle under the pushing force applied on the placement stylet 1000 mated to the device 700. As illustrated, rounded tip 702 and body 716 of miniature implantable 700 have exited the distal end 1002 of needle 900. The portions of body 716 that include electrodes 704 and electronic circuitry 706 are also shown on FIGS. 11B-11C. The proximal end 712 of miniature implantable 700 is mated to the distal end 1008 of placement stylet 1000. After the implantable 700 has been placed into a target region, the implantable device 700 may be sutured or anchored in place. Thereafter, the placement stylet 1000 may be unmated from the implanted 700. A clinician may then withdraw the placement stylet 1000 by pulling the placement stylet 1000 out of the patient's body through the needle 1000. The placement and withdrawal process may be performed under imaging guidance, such as, for example, X-Ray fluoroscopy, ultrasound fluoroscopy, etc. Once the procedure is completed, needle 900 may be removed.

Figure 12:
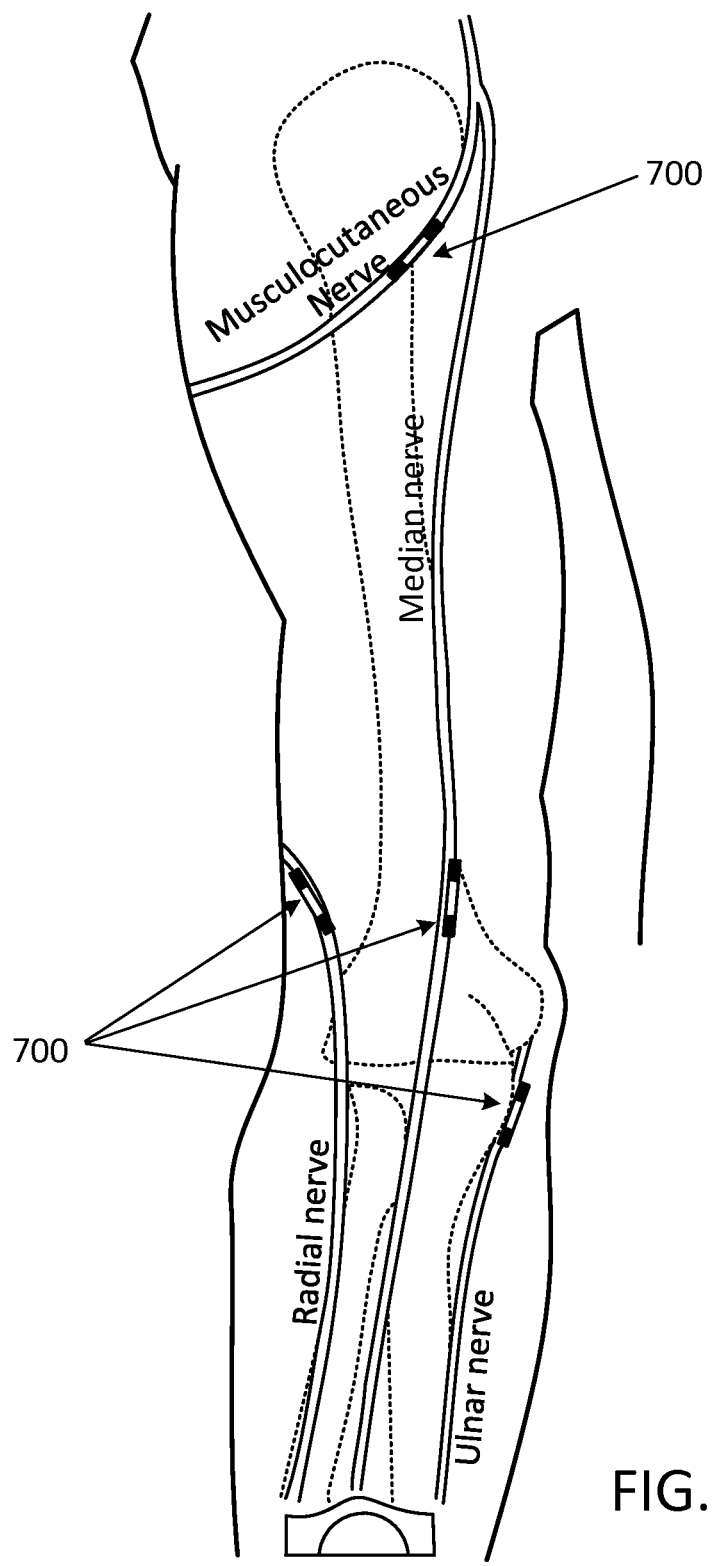
FIG. 12 illustrates the anatomical placement of four miniature implantable devices in the forearm.

FIG. 12 demonstrates the feasibility of placing multiple miniature implantable devices in the anatomical positions of the forearm. The compact size of the miniature implantable device 700 may allow minimally invasive placement procedure, thereby reducing complications during procedure and improving recovery time after procedure. Moreover, the compact size may allow multiple miniature implantable devices to be placed in nearby target areas. As shown in FIG. 12, four miniature implantable devices 700 are placed into the forearm of a patient, one in the upper forearm area and three in the lower forearm area. Each implanted lead may treat a specific nerve branch in the forearm region. Similarly, the miniature implantable devices 700 also may be delivered to treat a neural tissue branching from the spinal column including but not limited to the dorsal root ganglia, traversing, or exiting nerve. The miniature implantable devices 700 may also be delivered to treat peripheral nerve targets such as the radius, ulnar, sciatic, femoral, occipital, or brachial nerves. Given the compact size of the miniature leads, two or more such devices may be placed with pin-point precision to treat multiple nerve branches or peripheral nerve targets at the same time. In particular, two or more such devices may be placed with close proximity within a target area to provide pain-relief therapy to one or more excitable tissues within the target area. For instance, a patient may have one miniature implantable device 700 implanted adjacent to or near a target area. If more therapeutic effect is desired, the patient may have additional miniature implantable devices 700 implanted adjacent to or near the target area to enhance the therapeutic effect.

Figure 13A:
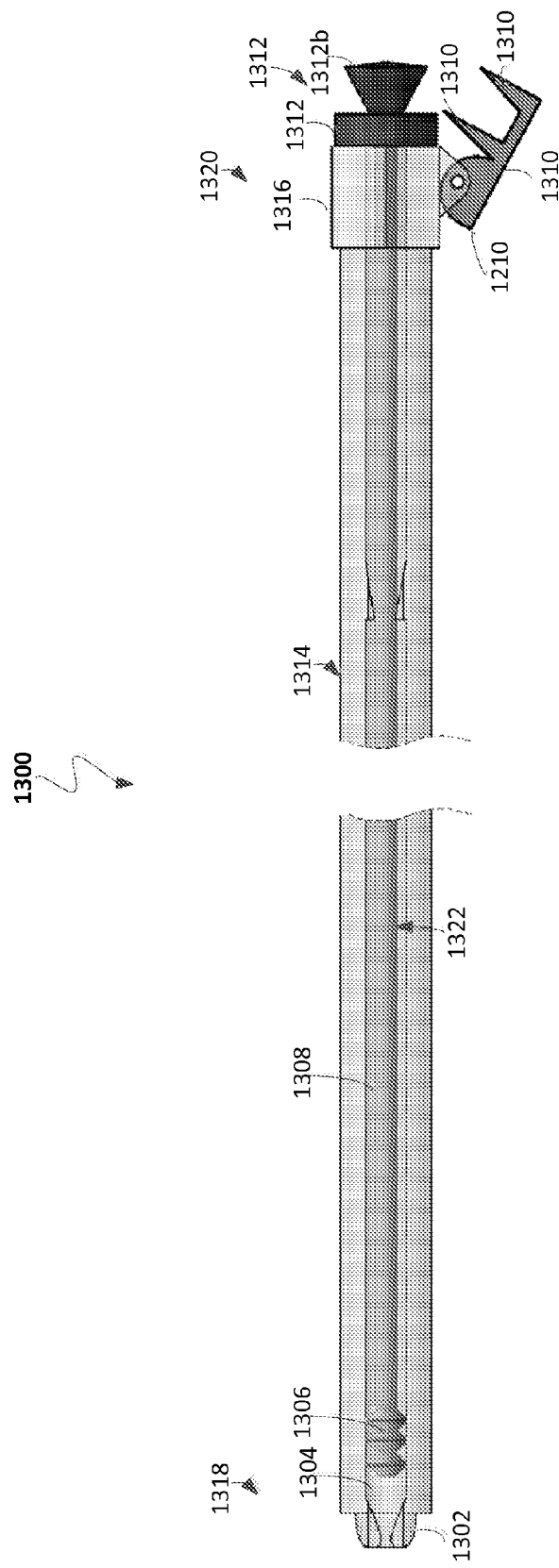
FIG. 13A illustrates an example suction stylet in zero pressure mode.

FIGS. 13A-13E illustrate a suction stylet 1300 in various modes of operation. The suction stylet 1300 is different from the placement stylet 1000 described above. As shown in FIG. 13A, the suction stylet 1300 is hollow inside and may have an outer diameter of between about 0.1 mm and 0.9 mm and may have a longitudinal length of between about 50 mm and 170 mm. The suction stylet 1300 may have an inner diameter between about 0.05 mm and 0.75 mm. The suction stylet 1300 includes distal end 1318, stylet body 1314, and proximal end 1316.

The distal end 1318 may include a mating feature 1302, chamber 1304, and plunger tip 1306. Mating feature 1302 also may be referred to as the suction tip. In some configurations, mating feature 1302 may be semi-spherical in shape and may have a diameter between about 0.05 mm and 0.08 mm. Mating feature 1302 on suction stylet 1300 may mate to mating feature 710 on miniature wireless lead 700, in a manner similar to the mechanical mating described above. In some instances, a mating force may be provided by a negative air pressure created inside air chamber 1304 on suction stylet 1300. In particular, by moving the plunger tip 1306 along the shaft for inner plunger 1308, a negative air pressure may be created in chamber 1304.

Stylet body 1314 may include inner plunger 1308 located inside shaft 1322. The inner plunger shaft 1322 may have a diameter between about 0.05 mm and 0.75 mm, allowing the plunger 1308 to slide inside of the hollow suction stylet 1300. The total length of the inner plunger including the inner plunger handle may be between about 50 mm and 170 mm. The inner plunger shaft, when installed, may not protrude beyond the suction tip.

The proximal end 1320 of suction stylet 1300 may include base 1316, handle 1312, and locking feature 1310. Base 1316 may have a diameter of between about 0.1 mm and 0.9 mm depending on the outer diameter of the hollow stylet 1300 being utilized. Handle 1312 may include cap 1312a and tip 1312b. Cap 1312a closes the tubing of suction stylet 1300. Handle tip 1312b may be pulled out during a placement procedure. The pulling may cause sliding motion of the plunger 1308 inside shaft 1322, which creates a negative air pressure in chamber 1304. Suction force may be created on suction tip, mating feature 1302, so that suction stylet 1300 is mated with miniature implantable device 700. Locking mechanism 1310 may include spike 1310a, spike 1310b, and hinge 1310c. Hinge 1310c is mounted on base 1316 and may rotate to engage spikes 1310a and 1310b with cap 1312a, as discussed below.

Figure 13B:
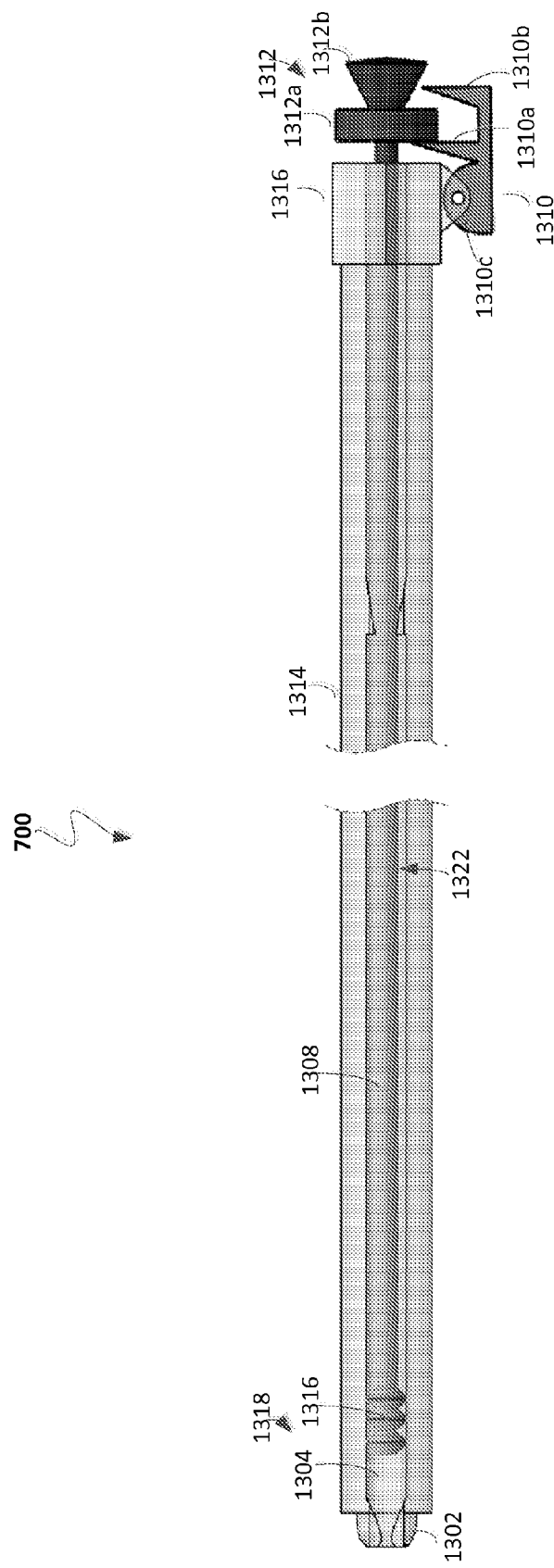
FIG. 13B illustrates the example suction stylet in first level of negative pressure mode.
Figure 13C:
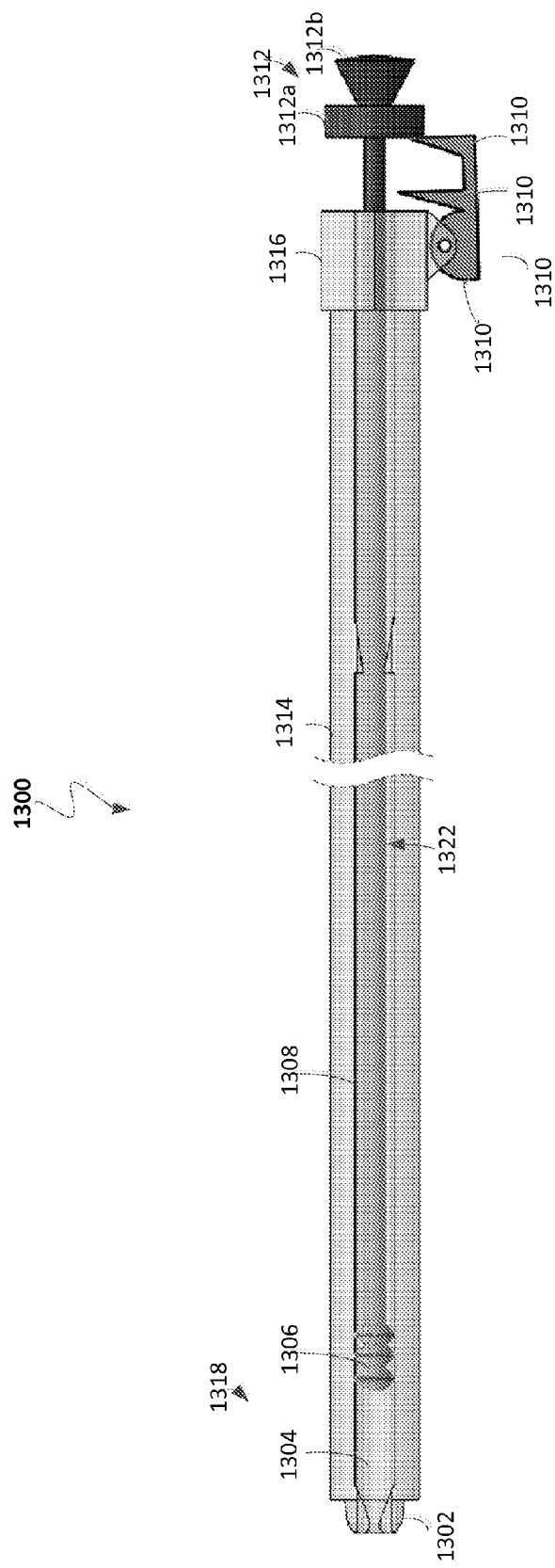
FIG. 13C illustrates the example suction stylet in second level of negative pressure mode.

FIGS. 13A to 13C show the suction stylet without the mating miniature implantable device. As illustrated, the inner plunger 1308 may be slid in a translating motion inside shaft 1322 to different locations within the hollow stylet 1300. Locking mechanism 1310 may be used to lock plunger 1308 into certain positions.

In particular, FIG. 13A shows the inner plunger 1308 in a complete seated condition with respect to the distal end 1320 of stylet 1300. In this position, no pressure differential may exist between the mating feature 1302 and plunger tip 1306.

Figure 13D:
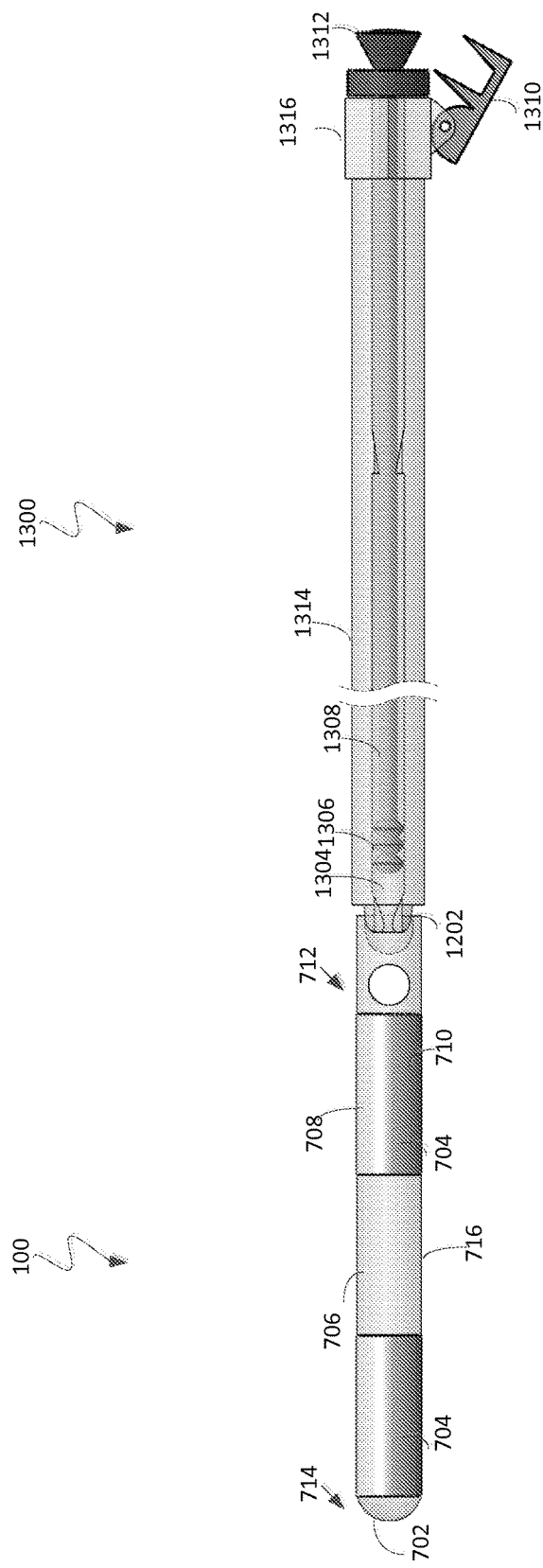
FIG. 13D illustrates an example miniature implantable device when the suction stylet is not active.

FIGS. 13B and 13D show the inner plunger 1308 at stage 1 position, which may be between about 1 mm and 10 mm from mating feature 1302 (suction tip) of the hollow stylet 1300. FIG. 13B shows suction stylet 1300 without the mated miniature implantable device 700, while FIG. 13D shows suction stylet 1300 mated with miniature implantable device 700. By pulling the handle tip 1312b away from the hollow stylet, a pressure differential may be generated to create a temporary mate between the miniature implantable device 700 and the stylet 1300. The mate is between mating feature 702 on miniature implantable device 700 and suction tip 1302 on suction stylet 1300. Locking mechanism 1310, as shown in FIG. 13B, may lock the inner plunger 1308 in place by engaging spike 1310a between base 1316 and cap 1312a. Once locked, the pressure differential between suction tip (mating feature 1302) and plunger tip 1306 may be maintained. This locking mechanism may be adjustable to allow for the inner plunger to be locked in a desired location.

Figure 13E:
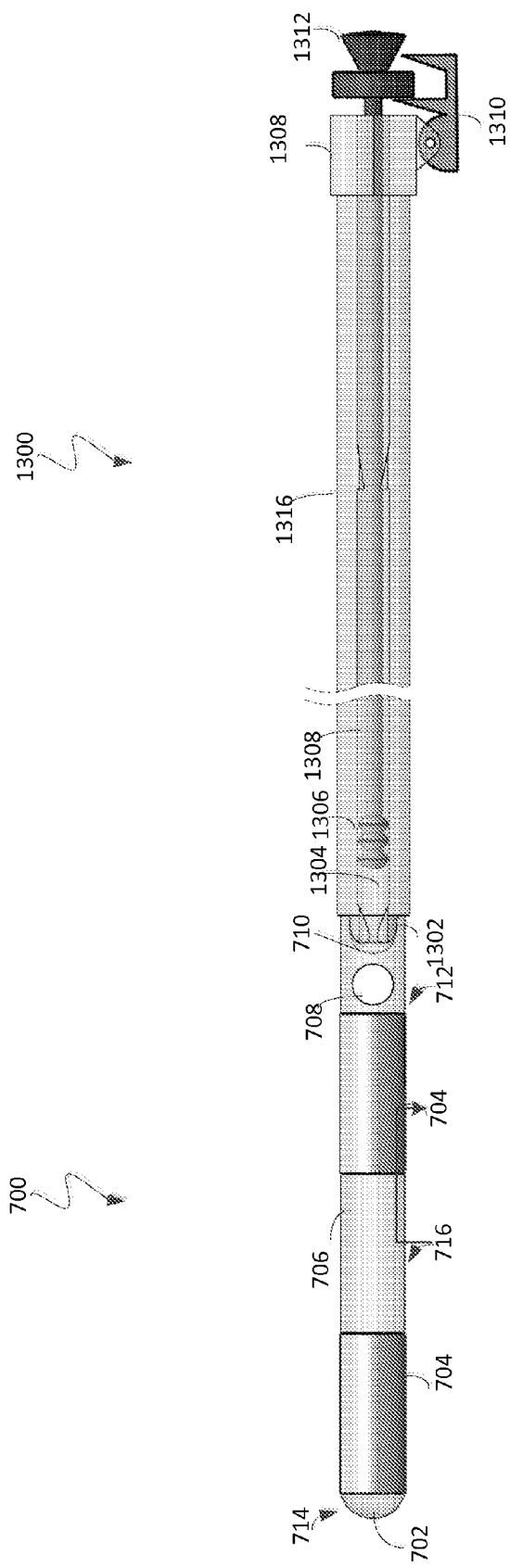
FIG. 13E illustrates an example miniature implantable device when the suction stylet is active.

FIGS. 13C and 13E illustrate the inner plunger 1308 being locked into a stage 2 location, which may be between about 2 mm and 30 mm from mating feature 1302 (suction tip) of the hollow stylet 1300. FIG. 13C shows suction stylet 1300 without the mated miniature implantable device 700, while FIG. 13E shows suction stylet 1300 mated with miniature implantable device 700. This stage may have a greater pressure differential generated than the stage 1 location depicted in FIG. 13B. In other examples, a suction stylet assembly may have one more locking stages depending on the locking mechanism utilized. An adjustable locking mechanism may allow for infinite locking distance locations.

The suction stylet design may provide the clinician the ability to install and remove the miniature implantable device 700 from a patient. As discussed above, once suction stylet 1300 is activated to engage miniature implantable device 700, an assembly of miniature implantable device 700 and suction stylet 1300 may be created. The clinician may push the suction stylet to advance the entire assembly, for example, down the inner lumen 904 of needle 900, towards the target site. If the miniature implantable device 700 is already implanted, the clinician can mate the miniature implantable device 700 to the suction tip of the stylet 1300, then pull on handle tip 1312*b*. Plunger 1308 may slide inside shaft 1322, thereby creating a pressure differential between suction tip 1302 and plunger tip 1306. The pressure differential may engage the miniature implantable device 700, and the clinician may withdraw the suction stylet 1300 to take the implanted lead 600 from within the patient.

Figure 14A:
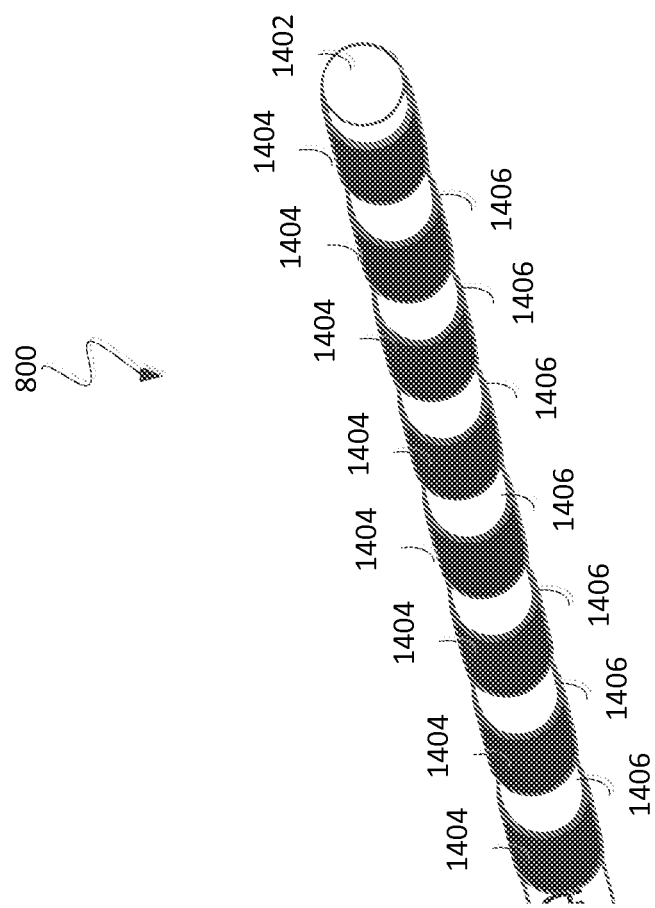
FIG. 14A illustrates a miniature implantable device with multiple recording or stimulating cylindrical electrode pads (eight shown).

FIG. 14A shows cylindrical electrodes 1404 (eight (8) shown) on the outside of a lead 1400. The outer diameter of lead 1400 may be 0.8 cm or smaller. Each cylindrical electrode 1404 may operate as a recording or stimulating electrode. A stimulating electrode may apply electric pulses to an excitable tissue to achieve therapeutic effect. A recording electrode may record or sense neural activity from surrounding tissue. In some instances, the electrodes may alternate between stimulating and recording electrodes. In the example shown, the miniature lead 1400 is not tethered and not connected to another structure or device for mechanical or electrical interface. One or more electrical flex circuitry may be internal to the miniature lead. The flex circuit may be inside gaps 1406, in between electrodes 1404. Lead 1400 may also include a rounded-tip 1402 for easy placement, as well as a mating feature to mate the lead 1400 with a stylet, such as those described above.

Figure 14B:
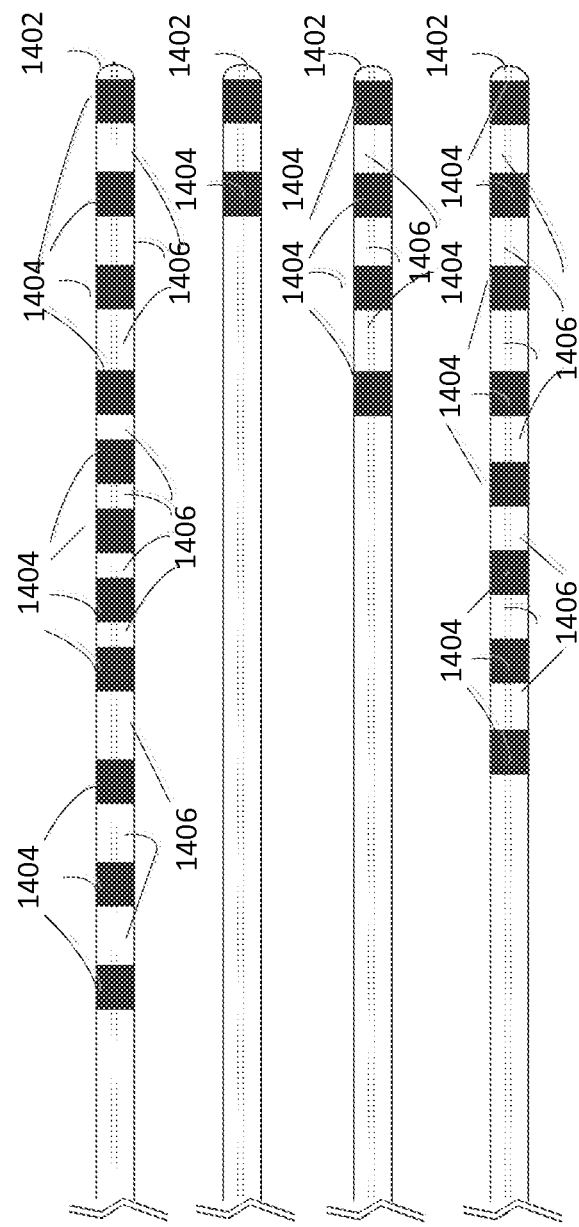
FIG. 14B illustrates various electrode configurations for stimulation and or recording electrodes on the miniature implantable device body, with various inter-electrode spacing options and mixture of recording and stimulation electrode assignments.

FIG. 14B shows four example miniature implantable devices incorporating multiple recording and/or stimulating electrodes 1404. The four example leads shown do not have an inner stylet lumen to mount a stylet or a guide wire, but may include a mating feature such as those described above. The recording and/or stimulating electrode pads 1404 may couple to a surrounding tissue for recording and/or stimulating. In a recording mode, neural activities of the surrounding tissue may be sensed and capture in electrical signals that encode such neural activities. In a stimulating mode, electric pulses may be applied to the surrounding tissue for pain relief. In some configurations, the electric circuitry may be spaced in between the recording and/or stimulating electrode pads, for example, in gaps 1406. As illustrated, example miniature implantable devices 1400 may include rounded tip 1402 for easy placement.

Figure 14C:
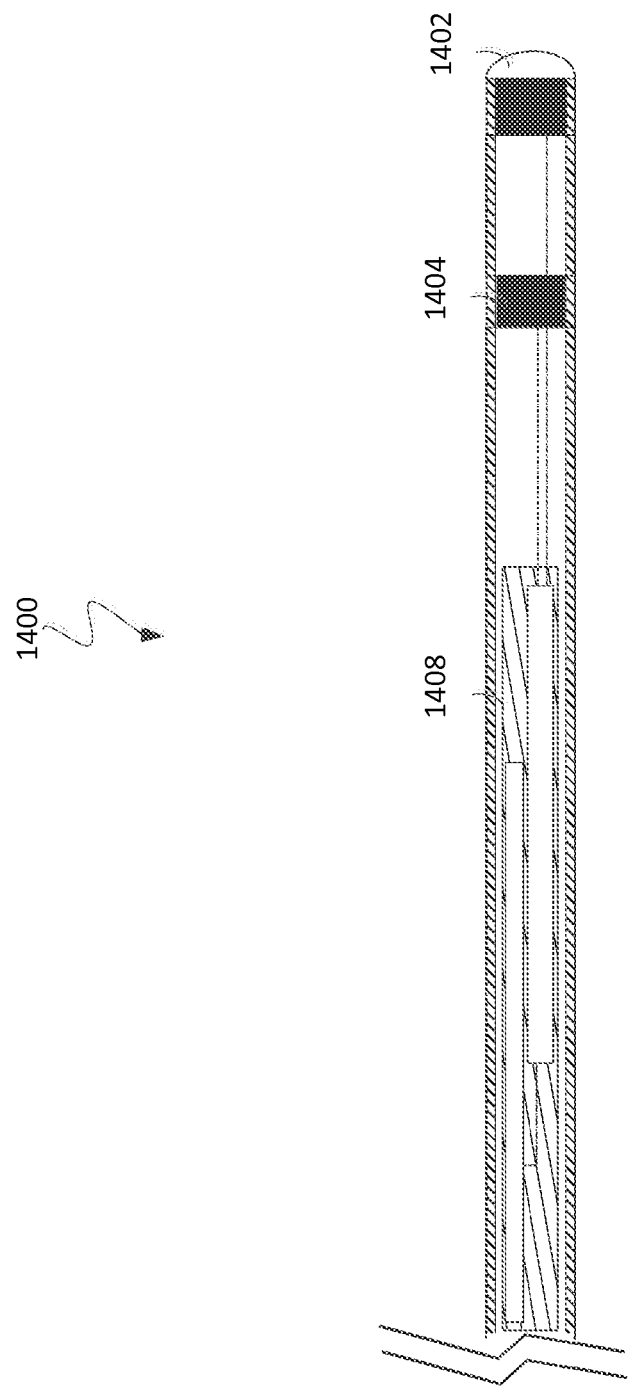
FIG. 14C is a cutout view of a miniature implantable device with stimulation or recording electrodes and the electronic circuitry and wireless power receiver.

FIG. 14C illustrates a miniature implantable device 1400 with stimulating and/or recording electrodes 1404 located at the distal end of the lead, in the direction of the rounded tip 1402. As illustrated, the electronic circuitry 1408 is located towards the proximal end of implantable device 1400, rather than spaced between the electrodes 1402.

For the configurations shown in FIGS. 14A to 14C, the electronic circuitry may provide power to drive the stimulating and/or recording electrodes. As described above, the electric pulses may be created by the electronic circuitry based on the input signal received at the antennas on the implantable devices. The electric pulses may be sent to a stimulating electrode to delivery pain-relief to an excitable tissue. As discussed above, a recording electrode may record neural activities of a surrounding tissue. The electronic circuitry also may route the recorded analog signal to the antennas on the implantable device which may in turn transmit the recorded analog signal to an external controller, located outside the patient body. In some implementations, the recorded analog signal may be processed and transmitted in a manner similar to the telemetry signal described above. For example, the transmission of the recorded analog signal, like the telemetry signal discussed herein, may be powered by the electrical power in the input signal.

Figure 15:
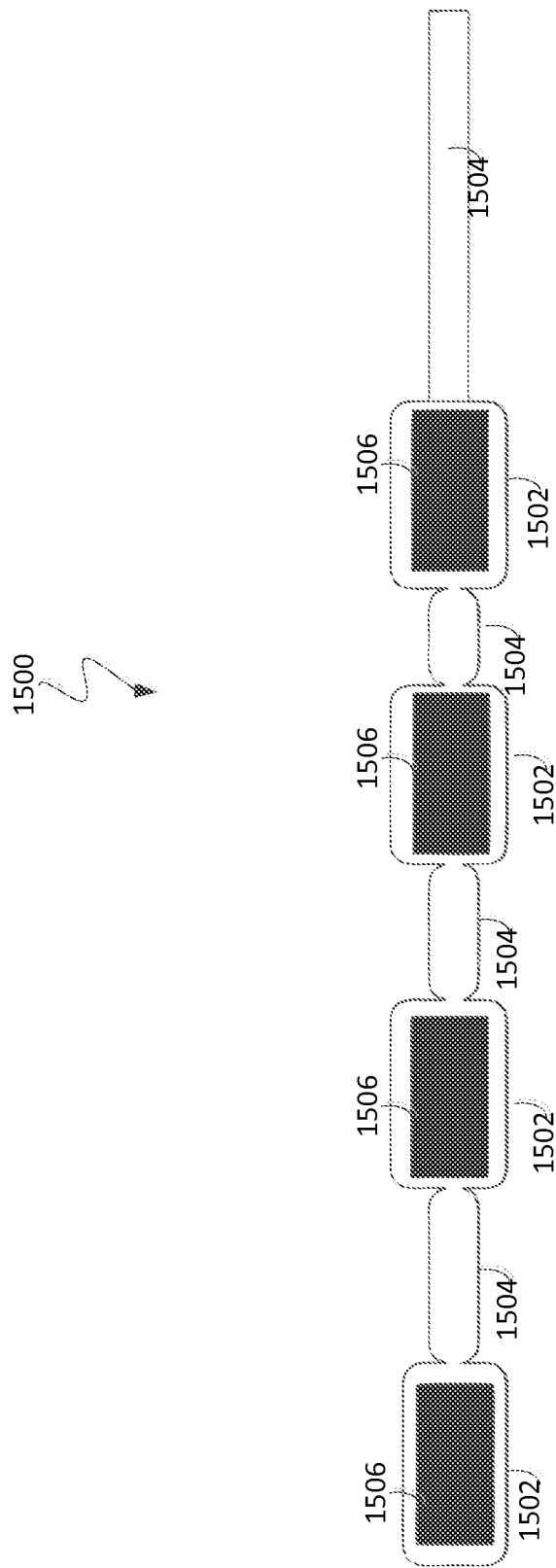
FIG. 15 illustrates a view of a miniature implantable device and a plate electrode configuration for the stimulation or recording pads.

FIG. 15 depicts an example of a lead 1500 with each electrode pad 1502 configured as a rectangular square. As illustrated, each rectangular square electrode pad 1502 may include an electrode 1506. Electronic circuitry may be located on structures 1504. Electrode 1506 may have a surface area of at least 0.06 mm2. This implantable device 1400 may have a total width from between about 0.5 mm and 0.8 mm. The height of the implantable device 1500 may be from between about 0.1 mm and about 0.8 mm. The total length of the implantable device 1500 may be from between about 10 mm and about 600 mm. The rectangular electrode pads 1502 may have a length from between about 0.5 mm and about 6.0 mm and a width from between about 0.45 mm and about 0.75 mm. The inter-electrode spacing may be from between about 0.1 mm and about 6.0 mm. This implantable device 1500 may be suitable for stimulating a relatively large area.

Figure 16:
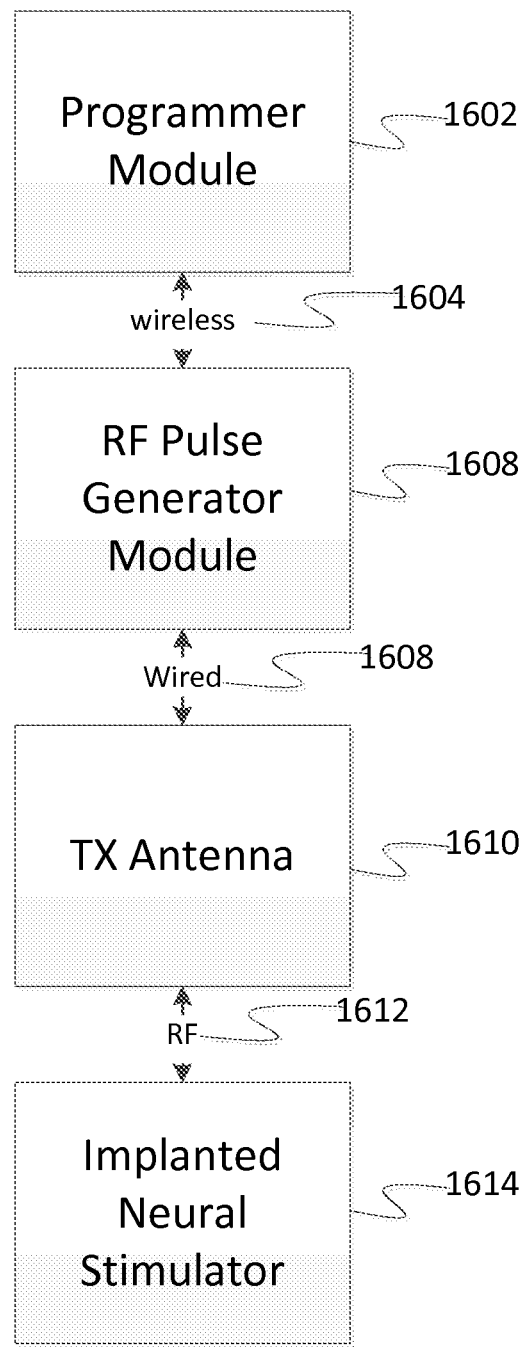
FIG. 16 depicts a high-level diagram of an example of a wireless neural stimulation system.
Figure 17:
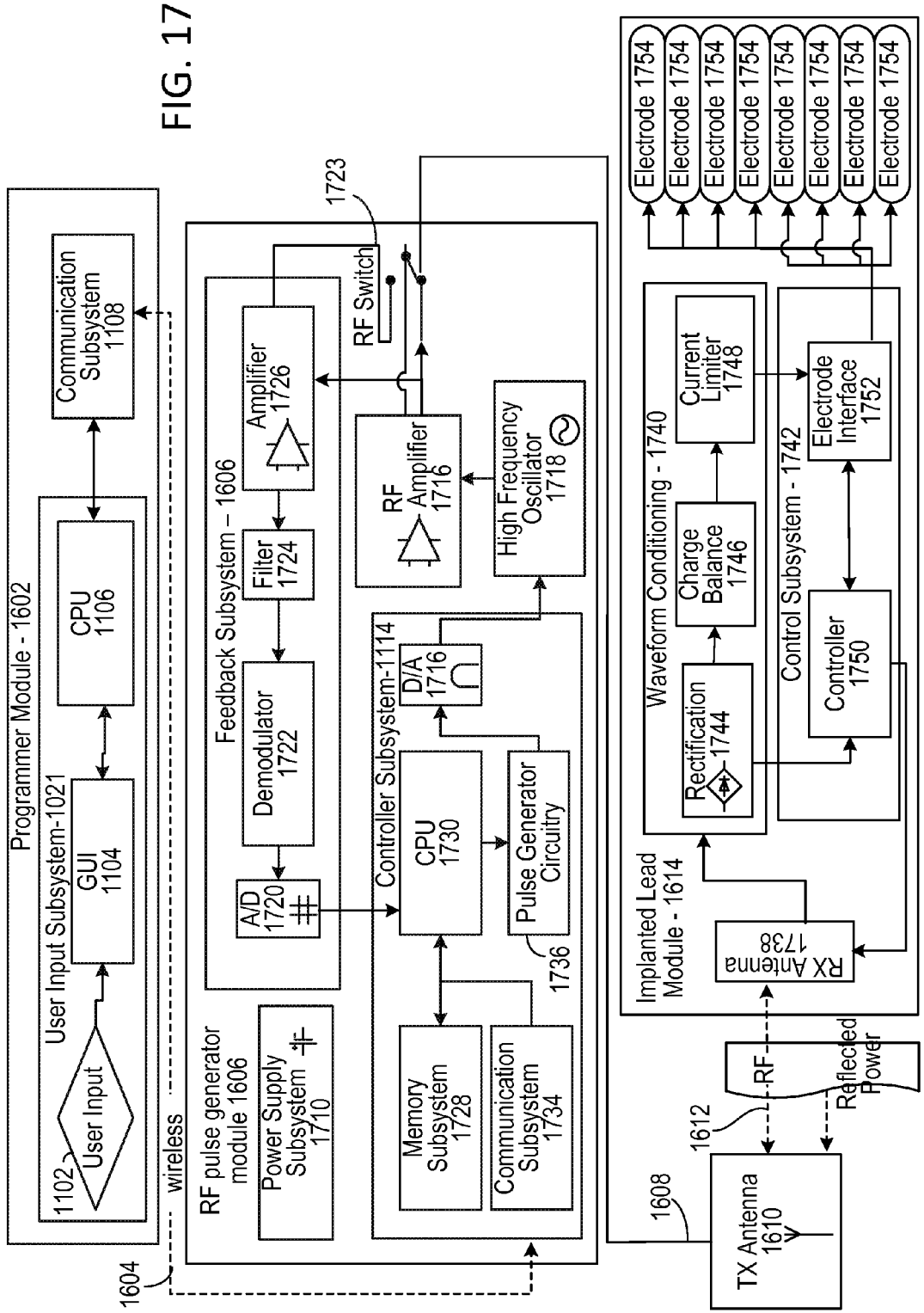
FIG. 17 depicts a detailed diagram of an example of a wireless neural stimulation system.

FIGS. 16 and 17 illustrate an example of a neural stimulation system that may employ the implantable devices described above. These implantable devices may also be referred to as implantable leads.

In particular, FIG. 16 depicts a high-level diagram of an example of a neural stimulation system. The neural stimulation system may include four major components, namely, a programmer module 1602, a RF pulse generator module 1606, a transmit (TX) antenna 1610 (for example, a patch antenna, slot antenna, or a dipole antenna), and an implanted device 1614, which may be a lead such as those described above. The programmer module 1602 may be a computer device, such as a smart phone, running a software application that supports a wireless connection 1614, such as Bluetooth®. The application can enable the user to view the system status and diagnostics, change various parameters, increase/decrease the desired stimulus amplitude of the electrode pulses, and adjust feedback sensitivity of the RF pulse generator module 1606, among other functions.

The RF pulse generator module 1606 may include communication electronics that support the wireless connection 1604, the stimulation circuitry, and the battery to power the generator electronics. In some implementations, the RF pulse generator module 1606 includes the TX antenna embedded into its packaging form factor while, in other implementations, the TX antenna is connected to the RF pulse generator module 1606 through a wired connection 1608 or a wireless connection (not shown). The TX antenna 1610 may be coupled directly to tissue to create an electric field that powers the implanted device 1614. The TX antenna 1610 communicates with the implanted device 1614 through an RF interface. For instance, the TX antenna 1610 radiates an RF transmission signal that is modulated and encoded by the RF pulse generator module 1610. The implanted device 1614 contains one or more antennas, such as dipole antenna(s), to receive and transmit through RF interface 1612. In particular, the coupling mechanism between antenna 1610 and the one or more antennas on the implanted device 1614 is electrical radiative coupling and not inductive coupling. In other words, the coupling is through an electric field rather than a magnetic field.

Through this electrical radiative coupling, the TX antenna 1610 can provide an input signal to the implanted device 1614. This input signal contains energy and may contain information encoding stimulus waveforms to be applied at the electrodes of the implanted device 1614. In some implementations, the power level of this input signal directly determines an applied amplitude (for example, power, current, or voltage) of the one or more electrical pulses created using the electrical energy contained in the input signal. Within the implanted device 1614 are components for demodulating the RF transmission signal, and electrodes to deliver the stimulation to surrounding neuronal tissue.

The RF pulse generator module 1606 can be implanted subcutaneously, or it can be worn external to the body. When external to the body, the RF generator module 1606 can be incorporated into a belt or harness design to allow for electric radiative coupling through the skin and underlying tissue to transfer power and/or control parameters to the implanted device 1614, which can be a passive stimulator. In either event, receiver circuit(s) internal to the device 1514 can capture the energy radiated by the TX antenna 1610 and convert this energy to an electrical waveform. The receiver circuit(s) may further modify the waveform to create an electrical pulse suitable for the stimulation of neural tissue, and this pulse may be delivered to the tissue via electrode pads.

In some implementations, the RF pulse generator module 1606 can remotely control the stimulus parameters (that is, the parameters of the electrical pulses applied to the neural tissue) and monitor feedback from the wireless device 1614 based on RF signals received from the implanted wireless device 1614. A feedback detection algorithm implemented by the RF pulse generator module 1606 can monitor data sent wirelessly from the implanted wireless device 1614, including information about the energy that the implanted wireless device 1614 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless device 1614 are monitored and used to determine the appropriate level of neural stimulation current for maintaining effective neuronal activation, or, in some cases, the patient can manually adjust the output signals in an open loop control method.

FIG. 17 depicts a detailed diagram of an example of the neural stimulation system. As depicted, the programming module 1602 may comprise user input system 1702 and communication subsystem 1708. The user input system 1721 may allow various parameter settings to be adjusted (in some cases, in an open loop fashion) by the user in the form of instruction sets. The communication subsystem 1708 may transmit these instruction sets (and other information) via the wireless connection 1604, such as Bluetooth or Wi-Fi, to the RF pulse generator module 1606, as well as receive data from module 1606.

For instance, the programmer module 1602, which can be utilized for multiple users, such as a patient's control unit or clinician's programmer unit, can be used to send stimulation parameters to the RF pulse generator module 1606. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
| --- | --- |
| Pulse Amplitude: | 0 to 20 mA |
| Pulse Frequency: | 0 to 20,000 Hz |
| Pulse Width: | 0 to 2 ms |

The implantable device 1614 or RF pulse generator module 1614 (which may be a lead such as those described above) may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 1602 may be functionally a smart device and associated application. The smart device hardware may include a CPU 1706 and be used as a vehicle to handle touchscreen input on a graphical user interface (GUI) 1704, for processing and storing data.

The RF pulse generator module 1606 may be connected via wired connection 1508 to an external TX antenna 1610. Alternatively, both the antenna and the RF pulse generator are located subcutaneously (not shown).

The signals sent by RF pulse generator module 1606 to the implanted device 1614 may include both power and parameter-setting attributes in regards to stimulus waveform, amplitude, pulse width, and frequency. The RF pulse generator module 1606 can also function as a wireless receiving unit that receives feedback signals from the implanted device 1614. To that end, the RF pulse generator module 1606 may contain microelectronics or other circuitry to handle the generation of the signals transmitted to the device 1614 as well as handle feedback signals, such as those from the device 1614. For example, the RF pulse generator module 1606 may comprise controller subsystem 1714, high-frequency oscillator 1718, RF amplifier 1716, a RF switch 1723, and a feedback subsystem 1712.

The controller subsystem 1714 may include a CPU 1730 to handle data processing, a memory subsystem 1728 such as a local memory, communication subsystem 1734 to communicate with programmer module 1602 (including receiving stimulation parameters from programmer module), pulse generator circuitry 1736, and digital/analog (D/A) converters 1732.

The controller subsystem 1714 may be used by the patient and/or the clinician to control the stimulation parameter settings (for example, by controlling the parameters of the signal sent from RF pulse generator module 1606 to device 1614). These parameter settings can affect, for example, the power, current level, or shape of the one or more electrical pulses. The programming of the stimulation parameters can be performed using the programming module 1602, as described above, to set the repetition rate, pulse width, amplitude, and waveform that will be transmitted by RF energy to the receive (RX) antenna 1738, typically a dipole antenna (although other types may be used), in the wireless implanted device 1714. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 1714 may store received parameter settings in the local memory subsystem 1728, until the parameter settings are modified by new input data received from the programming module 1602. The CPU 1706 may use the parameters stored in the local memory to control the pulse generator circuitry 1736 to generate a stimulus waveform that is modulated by a high frequency oscillator 1718 in the range from 300 MHz to 8 GHz. The resulting RF signal may then be amplified by RF amplifier 1726 and then sent through an RF switch 1723 to the TX antenna 1610 to reach through depths of tissue to the RX antenna 1738.

In some implementations, the RF signal sent by TX antenna 1610 may simply be a power transmission signal used by the device 1614 to generate electric pulses. In other implementations, a telemetry signal may also be transmitted to the device 1614 to send instructions about the various operations of the device 1614. The telemetry signal may be sent by the modulation of the carrier signal (through the skin if external, or through other body tissues if the pulse generator module 1606 is implanted subcutaneously). The telemetry signal is used to modulate the carrier signal (a high frequency signal) that is coupled onto the implanted antenna(s) 1738 and does not interfere with the input received on the same lead to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 1723 may be a multipurpose device such as a dual directional coupler, which passes the relatively high amplitude, extremely short duration RF pulse to the TX antenna 1610 with minimal insertion loss while simultaneously providing two low-level outputs to feedback subsystem 1712; one output delivers a forward power signal to the feedback subsystem 1712, where the forward power signal is an attenuated version of the RF pulse sent to the TX antenna 1610, and the other output delivers a reverse power signal to a different port of the feedback subsystem 1712, where reverse power is an attenuated version of the reflected RF energy from the TX Antenna 1610.

During the on-cycle time (when an RF signal is being transmitted to the device 1614), the RF switch 1723 is set to send the forward power signal to feedback subsystem. During the off-cycle time (when an RF signal is not being transmitted to the device 1614), the RF switch 1723 can change to a receiving mode in which the reflected RF energy and/or RF signals from the device 1614 are received to be analyzed in the feedback subsystem 1712.

The feedback subsystem 1712 of the RF pulse generator module 1606 may include reception circuitry to receive and extract telemetry or other feedback signals from the device 1614 and/or reflected RF energy from the signal sent by TX antenna 1610. The feedback subsystem may include an amplifier 1726, a filter 1724, a demodulator 1722, and an A/D converter 1720.

The feedback subsystem 1712 receives the forward power signal and converts this high-frequency AC signal to a DC level that can be sampled and sent to the controller subsystem 1714. In this way the characteristics of the generated RF pulse can be compared to a reference signal within the controller subsystem 1714. If a disparity (error) exists in any parameter, the controller subsystem 1714 can adjust the output to the RF pulse generator 1606. The nature of the adjustment can be, for example, proportional to the computed error. The controller subsystem 1714 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 1610 has perfectly matched impedance to the tissue that it contacts, the electromagnetic waves generated from the RF pulse generator 1606 pass unimpeded from the TX antenna 1610 into the body tissue. However, in real-world applications a large degree of variability may exist in the body types of users, types of clothing worn, and positioning of the antenna 1610 relative to the body surface. Since the impedance of the antenna 1610 depends on the relative permittivity of the underlying tissue and any intervening materials, and also depends on the overall separation distance of the antenna from the skin, in any given application there can be an impedance mismatch at the interface of the TX antenna 1610 with the body surface. When such a mismatch occurs, the electromagnetic waves sent from the RF pulse generator 1606 are partially reflected at this interface, and this reflected energy propagates backward through the antenna feed.

The dual directional coupler RF switch 1723 may prevent the reflected RF energy propagating back into the amplifier 1726, and may attenuate this reflected RF signal and send the attenuated signal as the reverse power signal to the feedback subsystem 1712. The feedback subsystem 1712 can convert this high-frequency AC signal to a DC level that can be sampled and sent to the controller subsystem 1714. The controller subsystem 1714 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 1714 can measure the reflected-power ratio in real time, and according to preset thresholds for this measurement, the controller subsystem 1714 can modify the level of RF power generated by the RF pulse generator 1606. For example, for a moderate degree of reflected power the course of action can be for the controller subsystem 1714 to increase the amplitude of RF power sent to the TX antenna 1610, as would be needed to compensate for slightly non-optimum but acceptable TX antenna coupling to the body. For higher ratios of reflected power, the course of action can be to prevent operation of the RF pulse generator 1606 and set a fault code to indicate that the TX antenna 1610 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless neural stimulator and thus cannot deliver therapy to the user.

The controller 1742 of the device 1614 may transmit informational signals, such as a telemetry signal, through the antenna 1738 to communicate with the RF pulse generator module 1606 during its receive cycle. For example, the telemetry signal from the device 1614 may be coupled to the modulated signal on the dipole antenna(s) 1738, during the on and off state of the transistor circuit to enable or disable a waveform that produces the corresponding RF bursts necessary to transmit to the external (or remotely implanted) pulse generator module 1606. The antenna(s) 1738 may be connected to electrodes 1754 in contact with tissue to provide a return path for the transmitted signal. An A/D (not shown) converter can be used to transfer stored data to a serialized pattern that can be transmitted on the pulse modulated signal from the internal antenna(s) 1738 of the neural stimulator.

A telemetry signal from the implanted wireless device 1614 may include stimulus parameters such as the power or the amplitude of the current that is delivered to the tissue from the electrodes. The feedback signal can be transmitted to the RF pulse generator module 1616 to indicate the strength of the stimulus at the nerve bundle by means of coupling the signal to the implanted RX antenna 1738, which radiates the telemetry signal to the external (or remotely implanted) RF pulse generator module 1606. The feedback signal can include either or both an analog and digital telemetry pulse modulated carrier signal. Data such as stimulation pulse parameters and measured characteristics of stimulator performance can be stored in an internal memory device within the implanted device 1614, and sent on the telemetry signal. The frequency of the carrier signal may be in the range of at 300 MHz to 8 GHz.

In the feedback subsystem 1712, the telemetry signal can be down modulated using demodulator 1722 and digitized by being processed through an analog to digital (A/D) converter 1720. The digital telemetry signal may then be routed to a CPU 1730 with embedded code, with the option to reprogram, to translate the signal into a corresponding current measurement in the tissue based on the amplitude of the received signal. The CPU 1730 of the controller subsystem 1714 can compare the reported stimulus parameters to those held in local memory 1728 to verify the stimulator(s) 1614 delivered the specified stimuli to tissue. For example, if the stimulator reports a lower current than was specified, the power level from the RF pulse generator module 1606 can be increased so that the implanted neural stimulator 1614 will have more available power for stimulation. The implanted neural stimulator 1614 can generate telemetry data in real time, for example, at a rate of 8 kbits per second. All feedback data received from the implanted lead module 1614 can be logged against time and sampled to be stored for retrieval to a remote monitoring system accessible by the health care professional for trending and statistical correlations.

The sequence of remotely programmable RF signals received by the internal antenna(s) 1738 may be conditioned into waveforms that are controlled within the implantable device 1614 by the control subsystem 1′742 and routed to the appropriate electrodes 1754 that are placed in proximity to the tissue to be stimulated. For instance, the RF signal transmitted from the RF pulse generator module 1606 may be received by RX antenna 1738 and processed by circuitry, such as waveform conditioning circuitry 1740, within the implanted wireless device 1614 to be converted into electrical pulses applied to the electrodes 1754 through electrode interface 1752. In some implementations, the implanted device 1614 contains between two to sixteen electrodes 1754.

The waveform conditioning circuitry 1740 may include a rectifier 1744, which rectifies the signal received by the RX antenna 1738. The rectified signal may be fed to the controller 1742 for receiving encoded instructions from the RF pulse generator module 1606. The rectifier signal may also be fed to a charge balance component 1746 that is configured to create one or more electrical pulses based such that the one or more electrical pulses result in a substantially zero net charge at the one or more electrodes (that is, the pulses are charge balanced). The charge-balanced pulses are passed through the current limiter 1748 to the electrode interface 1752, which applies the pulses to the electrodes 1754 as appropriate.

The current limiter 1748 insures the current level of the pulses applied to the electrodes 1754 is not above a threshold current level. In some implementations, an amplitude (for example, current level, voltage level, or power level) of the received RF pulse directly determines the amplitude of the stimulus. In this case, it may be particularly beneficial to include current limiter 1748 to prevent excessive current or charge being delivered through the electrodes, although current limiter 1748 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 1748 may act as a charge limiter that limits a characteristic (for example, current or duration) of the electrical pulses so that the charge per phase remains below a threshold level (typically, a safe-charge limit).

In the event the implanted wireless device 1714 receives a "strong" pulse of RF power sufficient to generate a stimulus that would exceed the predetermined safe-charge limit, the current limiter 1748 can automatically limit or "clip" the stimulus phase to maintain the total charge of the phase within the safety limit. The current limiter 1748 may be a passive current limiting component that cuts the signal to the electrodes 1754 once the safe current limit (the threshold current level) is reached. Alternatively, or additionally, the current limiter 1748 may communicate with the electrode interface 1752 to turn off all electrodes 1754 to prevent tissue damaging current levels.

A clipping event may trigger a current limiter feedback control mode. The action of clipping may cause the controller to send a threshold power data signal to the pulse generator 1606. The feedback subsystem 1712 detects the threshold power signal and demodulates the signal into data that is communicated to the controller subsystem 1714. The controller subsystem 1714 algorithms may act on this current-limiting condition by specifically reducing the RF power generated by the RF pulse generator, or cutting the power completely. In this way, the pulse generator 1606 can reduce the RF power delivered to the body if the implanted wireless neural stimulator 1614 reports it is receiving excess RF power.

The controller 1750 of the device 1705 may communicate with the electrode interface 1752 to control various aspects of the electrode setup and pulses applied to the electrodes 1754. The electrode interface 1752 may act as a multiplex and control the polarity and switching of each of the electrodes 1754. For instance, in some implementations, the wireless stimulator 1606 has multiple electrodes 1754 in contact with tissue, and for a given stimulus the RF pulse generator module 1606 can arbitrarily assign one or more electrodes to 1) act as a stimulating electrode, 2) act as a return electrode, or 3) be inactive by communication of assignment sent wirelessly with the parameter instructions, which the controller 1750 uses to set electrode interface 1752 as appropriate. It may be physiologically advantageous to assign, for example, one or two electrodes as stimulating electrodes and to assign all remaining electrodes as return electrodes.

Also, in some implementations, for a given stimulus pulse, the controller 1750 may control the electrode interface 1752 to divide the current arbitrarily (or according to instructions from pulse generator module 1606) among the designated stimulating electrodes. This control over electrode assignment and current control can be advantageous because in practice the electrodes 1754 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 1750, on its own or in response to instructions from pulse generator 1606, can control electrode interface 1752 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 1750 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 1750 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 1750 was configured to match the repetition rate for set B to that of set A, for such a case the controller 1750 can specify the relative start times of the stimulus cycles to be coincident in time or to be arbitrarily offset from one another by some delay interval.

In some implementations, the controller 1750 can arbitrarily shape the stimulus waveform amplitude, and may do so in response to instructions from pulse generator 1506. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 1750 can increase or decrease the level of current at any time during the stimulus phase and/or during the charge-balancing phase. Thus, in some implementations, the controller 1750 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the device 1614 may include a charge-balancing component 1746. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units of $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The device 1614 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 1746 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment of the present invention, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless device 1614 may create a drive-waveform envelope that follows the envelope of the RF pulse received by the receiving dipole antenna(s) 1738. In this case, the RF pulse generator module 1606 can directly control the envelope of the drive waveform within the wireless device 1614, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted device 1614 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 1606, and in others this control may be administered internally by circuitry onboard the wireless device 1614, such as controller 1750. In the case of onboard control, the amplitude and timing may be specified or modified by data commands delivered from the pulse generator module 1606.

A number of implementations have been described. Nevertheless, it will be understood that various modifications may be made. Accordingly, other implementations are within the scope of the following claims.

What is claimed is:

1. A method for treating a urological disorder in a patient, the method comprising:
   placing an introducer into a patient's body through an incision site on the patient's body to access one or more excitable tissue regulating a nerve activity associated with the urological disorder that the patient is suffering from;
   placing an implantable wireless device into an inner lumen of the introducer, the implantable wireless device suitable to fit into the inner lumen and configured to receive electromagnetic energy non-inductively from a source located outside the patient's body;
   through the inner lumen of the introducer, positioning the implantable wireless device adjacent to or near the one or more excitable tissue in the patient; and
   causing neural modulation of the one or more excitable tissue through one or more electrodes on the implantable wireless device where electrical stimulation is applied solely using the electromagnetic energy received non-inductively from the source outside the patient's body.

2. The method of claim 1, wherein placing the introducer comprises:
   placing the introducer through the incision site into a sacral region of the patient.

3. The method of claim 2, wherein positioning the implantable wireless device comprises: positioning the implantable wireless device adjacent to or near a sacral nerve of the patient.

4. The method of claim 1, wherein placing the introducer comprises placing the introducer through the incision site into a pelvic region of the patient.

5. The method of claim 4, wherein positioning the implantable wireless device comprises positioning the implantable wireless device adjacent to a pudendal nerve or branches thereof.

6. The method of claim 4, wherein positioning the implantable wireless device comprises positioning the implantable wireless device adjacent to or near a prostatic plexus of the patient.

7. The method of claim 4, wherein positioning the implantable wireless device comprises positioning the implantable wireless device adjacent to or near a sacral splanchnic nerve of the patient.

8. The method of claim 4, wherein positioning the implantable wireless device comprises positioning the implantable wireless device adjacent to or near a cavernous nerve of the patient.

9. The method of claim 1, wherein placing the introducer comprises placing the introducer percutaneously through an incision site on the patient's lower extremity.

10. The method of claim 9, wherein positioning the implantable wireless device comprises placing the implantable wireless device adjacent to or near a tibial nerve of the patient.

11. The method of claim 1, wherein placing the implantable wireless device further comprises placing the wireless electrode lead into the inner lumen of the introducer having a size of 14 gauge or under.

12. The method of claim 1, further comprising using X-Ray fluoroscopy to guide positioning the wireless electrode lead adjacent to or near one or more excitable tissue.

13. The method of claim 1, further comprising using ultrasound sonography to guide positioning the implantable wireless device adjacent to or near one or more excitable tissue.

14. The method of claim 1, further comprising withdrawing the implantable wireless device from the patient after the neural modulation.

15. The method of claim 1, wherein causing the neural modulation comprises:
- causing an input signal to be transmitted from an external antenna outside the patient's body, the input signal including electrical power and excitation pulses to drive the one or more electrodes of the implantable wireless device;
- causing the input signal to be received non-inductively by one or more antennas on the implantable wireless device;
- causing the electrical power and excitation pulses to be extracted from the input signal; and
- based on the extracted electrical power, causing the excitation pulses to be delivered to the one or more electrodes on the implantable wireless device.

16. The method of claim 1, wherein placing an implantable wireless device further comprises placing a implantable wireless device that includes (i) one or more non-inductive antennas configured to receive electromagnetic energy radiated from a source located outside of the patient's body, (ii) electronic circuitry coupled to each of the one or more non-inductive antennas and configured to extract electric power and excitation pulses from the radiated electromagnetic energy as received by the one or more non-inductive antennas, and (iii) one or more electrodes configured to deliver the excitation pulses to the one or more excitable tissue to effectuate neural modulation thereof.

17. The method of claim 16, wherein placing the implantable wireless device further comprises placing the implantable wireless device that includes at least one of: a spiral electrode, a cuff electrode, a steroid eluting electrode, a wrap-around electrode, a linear electrode, or a hydrogel electrode.

* * * * *

UNITED STATES PATENT AND TRADEMARK OFFICE
CERTIFICATE OF CORRECTION

PATENT NO. : 9,623,253 B2
APPLICATION NO. : 14/775429
DATED : April 18, 2017
INVENTOR(S) : Laura Tyler Perryman and Chad Andresen It is certified that error appears in the above-identified patent and that said Letters Patent is hereby corrected as shown below:

In the Specification

Column 1, Line 5, delete "61/786,098," and insert -- 61/786,181, --, therefor.

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*